(12) United States Patent
Degertekin et al.

(10) Patent No.: US 11,950,854 B2
(45) Date of Patent: Apr. 9, 2024

(54) ACOUSTO-OPTICAL ACTIVE MARKERS FOR INTERVENTIONAL MRI

(71) Applicant: Georgia Tech Research Corporation, Atlanta, GA (US)

(72) Inventors: Fahrettin Levent Degertekin, Atlanta, GA (US); Ozgur Kocaturk, Rockville, IL (US); Yusuf S. Yaras, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 474 days.

(21) Appl. No.: 17/258,806

(22) PCT Filed: Jul. 9, 2019

(86) PCT No.: PCT/US2019/041011
§ 371 (c)(1),
(2) Date: Jan. 8, 2021

(87) PCT Pub. No.: WO2020/014230
PCT Pub. Date: Jan. 16, 2020

(65) Prior Publication Data
US 2021/0267696 A1  Sep. 2, 2021

Related U.S. Application Data

(60) Provisional application No. 62/695,235, filed on Jul. 9, 2018.

(51) Int. Cl.
*A61B 34/20* (2016.01)
*A61B 5/00* (2006.01)
(Continued)

(52) U.S. Cl.
CPC ............ *A61B 34/20* (2016.02); *A61B 5/0097* (2013.01); *A61B 5/05* (2013.01); *A61B 5/055* (2013.01);
(Continued)

(58) Field of Classification Search
CPC ......... A61B 34/20; A61B 5/0097; A61B 5/05; A61B 5/055; A61B 5/065; A61B 90/39;
(Continued)

(56) References Cited

U.S. PATENT DOCUMENTS 4,068,191 A * 1/1978 Zemon .................. G02F 1/0134
372/27
2003/0135110 A1 7/2003 Leussler
(Continued)

OTHER PUBLICATIONS

Search Report and Written Opinion from Application No. PCT/US2019/041011 dated Sep. 26, 2019 (12 pages).

*Primary Examiner* — Rochelle D Turchen
(74) *Attorney, Agent, or Firm* — Troutman Pepper Hamilton Sanders LLP; Ryan A. Schneider; Mark Lehi Jones

(57) ABSTRACT

Certain implementations of the disclosed technology may include active marker devices, retrofits, systems, and methods for determining the position of interventional devices under MRI. A marker device is provided that utilizes an optical fiber, an acousto-optical sensor region that includes an electro-mechanical conversion assembly, and one or more antenna(e) The one or more antennae are configured to receive MRI radio-frequency (RF) electromagnetic energy and produce a corresponding electrical signal corresponding to the position. The acousto-optical sensor region may include a resonator and may be modulated by acoustic waves generated responsive to the electrical signal received from the one or more antennae The acousto-optical sensor (Continued)

region may be interrogated by light via the optical fiber to determine the position of the device for providing an active marker in the MRI image.

28 Claims, 12 Drawing Sheets

(51) Int. Cl.
| | |
|---|---|
| *A61B 5/05* | (2021.01) |
| *A61B 5/055* | (2006.01) |
| *A61B 5/06* | (2006.01) |
| *A61B 90/00* | (2016.01) |
| *A61M 25/01* | (2006.01) |
| *G01R 33/28* | (2006.01) |
| *G01R 33/36* | (2006.01) |

(52) U.S. Cl.
CPC .............. *A61B 5/065* (2013.01); *A61B 90/39* (2016.02); *A61M 25/0105* (2013.01); *G01R 33/287* (2013.01); *G01R 33/3692* (2013.01); *A61B 2034/2051* (2016.02); *A61B 2034/2061* (2016.02); *A61B 2034/2063* (2016.02); *A61B 2090/3958* (2016.02); *A61B 2090/3987* (2016.02); *A61M 25/0108* (2013.01)

(58) Field of Classification Search
CPC .... A61B 2034/2051; A61B 2034/2061; A61B 2034/2063; A61B 2090/3958; A61B 2090/3987; A61M 25/0105; A61M 25/0108; G01R 33/287; G01R 33/3692
See application file for complete search history.

(56) References Cited

U.S. PATENT DOCUMENTS

| | | | |
|---|---|---|---|
| 2004/0073171 | A1 | 4/2004 | Rogers et al. |
| 2009/0326560 | A1 | 12/2009 | Lampropoulos et al. |
| 2010/0022868 | A1* | 1/2010 | Kocaturk ............. G01R 33/287 |
| | | | 600/463 |
| 2011/0163922 | A1 | 7/2011 | Wang et al. |
| 2017/0143234 | A1 | 5/2017 | Degertekin et al. |
| 2018/0256237 | A1* | 9/2018 | Fan ................... A61B 1/00101 |

* cited by examiner

ACOUSTO-OPTICAL ACTIVE MARKERS FOR INTERVENTIONAL MRI

CROSS-REFERENCE TO RELATED APPLICATIONS

This application claims priority to U.S. Provisional Patent Application No. 62/695,235, entitled "Acousto-optical Markers for Interventional MRI," filed 9 Jul. 2018, the contents of which are also incorporated by reference in their entirety as if set forth in full. This application is also related to U.S. patent application Ser. No. 15/303,002, entitled "Interventional MRI Compatible Medical Device, System, and Method," filed 10 Apr. 2015, and published as U.S. Patent Publication No. US2017/0143234 on 25 May 2017, the contents of which are also incorporated by reference in their entirety as if set forth in full.

GOVERNMENT SUPPORT

This invention was made with government support under Grant No. EB017365 awarded by the National Institutes of Health. The government has certain rights in the invention.

FIELD

The disclosed technology relates generally to MRI compatible devices, and more specifically to active marker devices for interventional device visualization under MRI.

BACKGROUND

Magnetic resonance imaging (MRI) is a medical imaging technique to non-invasively create detailed images of the tissues, fluids, bone, implants, etc., within a body based on the specific physical and biochemical properties. MRI provides certain advantages over traditional medical imaging techniques, including the ability to obtain high-contrast images with excellent delineation of anatomic structures, while avoiding ionizing radiation. The ability to obtain images in multiple planes through body parts makes MRI an important medical diagnostic tool.

A specialized growing subset of interventional MRI is intraoperative MRI, in which an MRI is used in aiding surgery. However, the use of simultaneous MRI imaging during interventional surgery has been limited due to a lack of safe and conspicuous catheter devices. For example, one safety risk associated with MRI is the RF-induced heating that can result from an interaction between the pulsed electromagnetic RF field of the MRI scanner and the catheter device, as discussed in "Investigation of the factors responsible for burns during MRI," Dempsey et al, Journal of Magnetic Resonance Imaging, vol. 13, pp. 627-631, which is incorporated herein by reference. Such risks can be minimized or eliminated if the catheter device is free of elongated conductive structures such as leads, electrodes, and/or guidewires.

A challenge associated with intraoperative MRI is the visibility of the catheter during a procedure in real-time. It is important to know the location of the catheter's distal tip to safely navigate vascular structures. For example, as a medical device is advanced through the patient's body during a procedure, it is desirable to track the probe's location so that the device can be properly delivered to a target site. Conventionally, this is achieved by embedding active and/or passive markers into the device shaft. But prior active markers use conductive transmission lines to carry the received RF signal from the distal end of the probe to the MR scanner, which can result in RF-induced heating. It would be desirable to provide spatial position and/or temperature information of the catheter tip and/or shaft to guide the interventional procedures. As different pre-shaped catheters are used for different procedures, it is desirable to have a sensor with a universal package that can be quickly adapted over different catheters in clinical-use settings.

U.S. Patent Publication No. US2017/0143234, which is incorporated herein by reference in its entirety, discloses a clinical-grade active catheter device for active device visualization under MRI and provides certain solutions to address the risk of RF-induced heating. However, once a catheter assembly is manufactured without the benefit of acceptable visualization (or location marker) technology, the use of such tool may be limited to applications in which the probe remains stationary (or is removed) during MRI imaging.

Certain exemplary implementations are disclosed herein to address the above-referenced risks, challenges, and limitations.

BRIEF SUMMARY

Briefly described, certain exemplary implementations of the disclosed technology include active markers to determine the position of interventional devices under MRI. Certain exemplary implementations of the disclosed technology can include catheter devices, retrofit devices, and systems including the active markers for device visualization under MRI. Some or all of the above needs may be addressed by certain implementations of the disclosed technology.

Certain implementations of the disclosed technology may include active marker devices, retrofits, systems, and methods for determining the position of interventional devices under MRI. A marker device is provided that utilizes an optical fiber, an acousto-optical sensor region that includes an electro-mechanical conversion assembly, and one or more antenna(e). The one or more antennae are configured to receive MRI radio-frequency (RF) electromagnetic energy and produce a corresponding electrical signal corresponding to the position. The acousto-optical sensor region may include a resonator and may be modulated by acoustic waves generated responsive to the electrical signal received from the one or more antennae. The acousto-optical sensor region may be interrogated by light via the optical fiber to determine the position of the device for providing an active marker in the MRI image Certain implementations may include a catheter retrofit device for active MRI device location visualization. The retrofit device can include a mounting tube configured to accept a catheter and to a least partially conform to a shape of the catheter; an optical fiber including a distal end in communication with a portion of the mounting tube structure; an acousto-optical sensor region disposed at the distal end of the optical fiber, the acousto-optical sensor region including an electro-mechanical conversion assembly that includes one or more antennae disposed on the mounting tube structure, the one or more antennae configured to receive radio-frequency (RF) electromagnetic energy and produce a corresponding electrical signal; and an ultrasonic transducer in mechanical communication with the acousto-optical sensor region, wherein the ultrasonic transducer is in electrical communication with the one or more antennae, and wherein the ultrasonic transducer is configured to elastically modulate the acousto-optical sensor region by acoustic waves generated responsive to the electrical signal received from the one or more antennae.

According to another exemplary implementation, a catheter retrofit system is provided for MRI active device location visualization. The system can include a retrofitted interventional probe that includes: a mounting tube configured to accept a catheter and to a least partially conform to a shape of the catheter; an optical fiber including a distal end in communication with a portion of the mounting tube structure; an acousto-optical sensor region disposed at the distal end of the optical fiber, the acousto-optical sensor region including an electro-mechanical conversion assembly that includes one or more antennae disposed on the mounting tube structure, the one or more antennae configured to receive radio-frequency (RF) electromagnetic energy and produce a corresponding electrical signal; and an ultrasonic transducer in mechanical communication with the acousto-optical sensor region, wherein the ultrasonic transducer is in electrical communication with the one or more antennae, and wherein the ultrasonic transducer is configured to elastically modulate the acousto-optical sensor region by acoustic waves generated responsive to the electrical signal received from the one or more antennae. The catheter retrofit system can include a mechanical-optical conversion assembly in communication with a proximal end of the optical fiber, the mechanical-optical conversion assembly can include: a light source coupled to the proximal end of the optical fiber and configured to interrogate the acousto-optical sensor region; and a photodetector coupled to the proximal end of the optical fiber, the photodetector configured to receive interrogation light reflected from the acousto-optical sensor region.

According to another exemplary implementation, a catheter is provided for MRI active device location visualization. The catheter can include an optical fiber including a distal end; an acousto-optical sensor region disposed at the distal end of the optical fiber, the acousto-optical sensor region including an electro-mechanical conversion assembly that includes one or more antennae disposed on the mounting tube structure, the one or more antennae configured to receive radio-frequency (RF) electromagnetic energy and produce a corresponding electrical signal; and an ultrasonic transducer in mechanical communication with the acousto-optical sensor region, wherein the ultrasonic transducer is in electrical communication with the one or more antennae, and wherein the ultrasonic transducer is configured to elastically modulate the acousto-optical sensor region by acoustic waves generated responsive to the electrical signal received from the one or more antennae.

According to another exemplary implementation, a marker is provided for MRI active device location visualization. The marker can include an optical fiber including a distal end; an acousto-optical sensor region disposed at the distal end of the optical fiber, the acousto-optical sensor region including an electro-mechanical conversion assembly that includes one or more antennae disposed on the mounting tube structure, the one or more antennae configured to receive radio-frequency (RF) electromagnetic energy and produce a corresponding electrical signal; and an ultrasonic transducer in mechanical communication with the acousto-optical sensor region, wherein the ultrasonic transducer is in electrical communication with the one or more antennae, and wherein the ultrasonic transducer is configured to elastically modulate the acousto-optical sensor region by acoustic waves generated responsive to the electrical signal received from the one or more antennae. The acousto-optical sensor region also includes an acoustic resonator to enhance the sensitivity of the device. The marker can be physically attached to any other device, such as a catheter tip to visualize and provide quantitative location information under the MRI.

According to an exemplary implementation, a method is provided for retrofitting a catheter with a marker device. The method can include providing the catheter retrofit marker device, sliding the device onto a catheter to a first position and securing the device to at least a portion of the catheter Other implementations, features, and aspects of the disclosed technology are described in detail herein and are considered a part of the claimed disclosed technology. Other implementations, features, and aspects can be understood with reference to the following detailed description, accompanying drawings, and claims.

BRIEF DESCRIPTION OF THE FIGURES

Reference will now be made to the accompanying figures and flow diagrams, which are not necessarily drawn to scale, and wherein.

DETAILED DESCRIPTION

Figure 1:
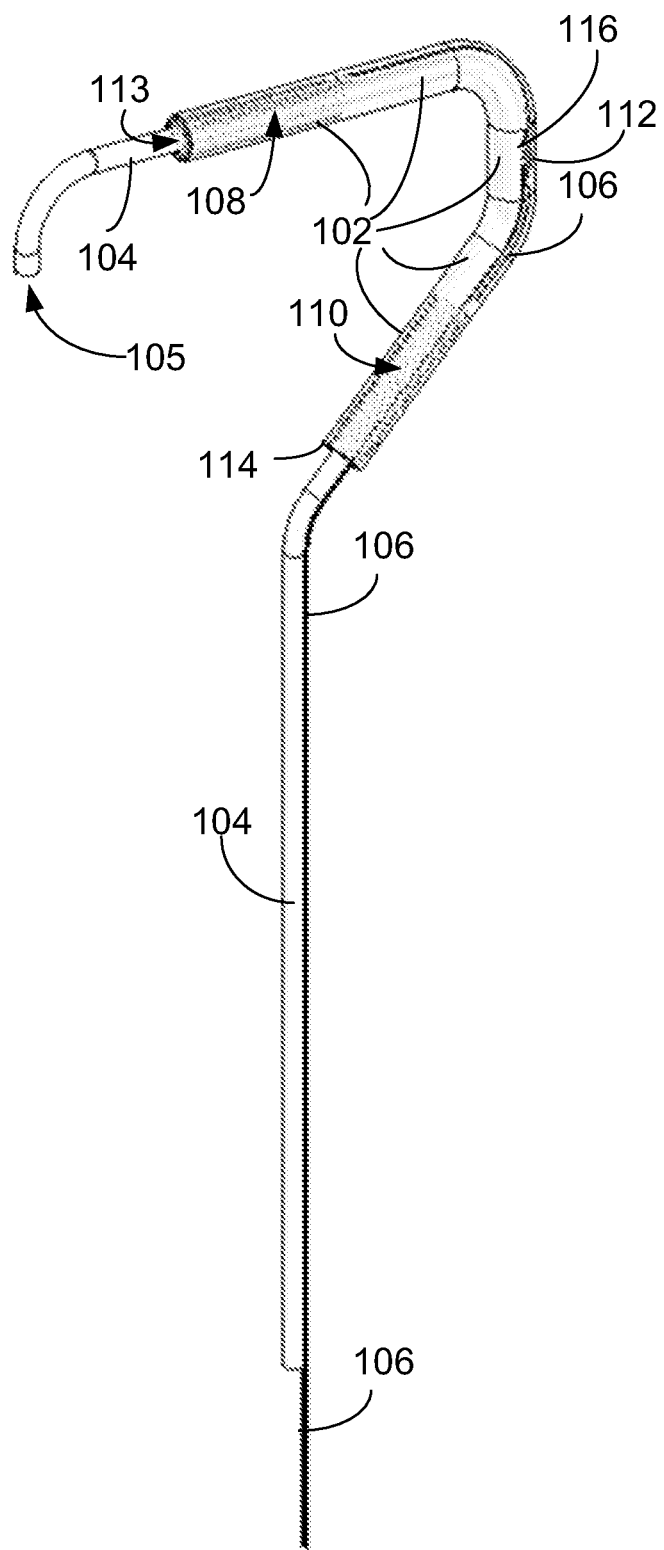
FIG. 1 is an illustration of an acousto-optical based sleeve marker retrofit device disposed over a conventional diagnostic catheter, according to an exemplary embodiment of the disclosed technology.

The disclosed technology relates to certain advancements and improvements in an acousto-optical marker device for safe clinical operation and location tracking of a catheter in interventional magnetic resonance imaging (MRI) applications. Certain aspects of the disclosed technology are related to U.S. Patent Publication No. US2017/0143234, the contents of which is incorporated by reference in its entirety as if set forth in full.

U.S. Patent Publication No. US2017/0143234 describes an acousto-optical (AO) catheter probe incorporating an active receiver that can modulate interrogation light at a frequency of the localized MRI gradient field. The reflected and modulated light can be utilized to determine the location of the probe. The probe can include a receiver coil in communication with a piezoelectric transducer that is coupled to an acousto-optical sensor region of an optical fiber. For example, the acousto-optical sensor region can include a fiber Bragg grating (FBG). The optical fiber serves as a transmission line that enables the elimination of typically elongated lead wire conductors that can heat up (and damage surrounding tissue) in the presence of the MRI equipment's electromagnetic RF field. The piezoelectric transducer is directly in contact with the optical fiber over the FBG region and generates acousto-optical modulation signals directly on the fiber. Using a thin film piezoelectric layer directly deposited on the fiber partially or fully over the circumference, the elastic waves generated by the piezoelectric layer may be cylindrically focused on the core of the optical fiber where it is most effective. This technique presents efficient AO modulation at a target frequency for locating the receiver coil position.

The disclosed technology includes certain advancements and improvements, that when combined with the technology disclosed in U.S. Patent Publication No. US2017/0143234 may be utilized to produce an improved device that can address certain challenges, limitations, and issues associated with prior devices.

Certain improvements disclosed herein can include: (1) a universal sleeve package that can be quickly adapted over different catheters in clinical-use settings; (2) multiple antennae sensors to provide enhanced catheter location, orientation, and associated RF field components; (3) acoustic resonator structures to improve the sensitivity of the AO sensors; and (4) orthogonal coils for enhanced marking or RF field vector mapping.

Certain elements of the disclosed technology may further utilize one or more of electrical-to-mechanical energy conversion via a piezoelectric transducer for receiver signal extraction, acousto-optical modulation on the fiber for mechanical-to-optical signal conversion, increased signal sensitivity via an FBG, and robust optical fibers for signal transmission and detection. The resulting combination may yield retrofit and/or other improved devices that can include MRI safe active receivers and location markers without conducting transmission lines and without compromising mechanical performance.

FIG. 1 is an illustration of an acousto-optical sleeve marker retrofit device 102 installed over a conventional diagnostic catheter 104, according to an exemplary embodiment of the disclosed technology. (Refer to the explanation provided below with reference to FIG. 4A and FIG. 4B below for additional details on the theory of operation of the device 102). In certain exemplary implementations, the catheter 104 may be threaded (for example, starting with the distal end 105) into an opening 113 of the retrofit device 102 that can extend axially through its entire length. In certain exemplary implementations, the one or more receiver antennae 108, 110 may be positioned at the desired location for visibility of the catheter 104 under MRI.

In certain implementations, an optical fiber 106 of the device 102 may be coupled to a fiber Bragg grating (FBG) 116, which may be in contact with a piezoelectric transducer 112 that is driven by the one or more receiver antennae 108, 110. The optical fiber 106 may extend from the FBG 116, along the catheter 104, and out the proximal end to an external light source (such as a swept laser) and a detector. In certain implementations, the retrofit device 102 may include at least an outer flexible heat-shrinkable tube 114 that may be utilized to secure the sleeve marker retrofit device 102 to the desired position on the catheter 104, for example, by application of heat using a heat gun. Once installed, the tube 114 may also serve as a protective layer for the various components of the retrofit device 102. In certain exemplary implementations, the optical fiber 106 may also be secured to the catheter 104 shaft along its length using a similar heat shrinkable tube and/or a continuing portion of the tube 114 (not shown). In certain exemplary implementations, the end portions of the tube 114 may be beveled or shaped to prevent such ends from catching or binding during insertion into a patient.

Certain exemplary implementations of the disclosed technology can be manufactured directly into a catheter, for example, without requiring certain retrofit components, such as the heat-shrink tubing as discussed above. Rather, in certain exemplary implementations, the catheter body itself may be utilized for housing/mounting/protecting the associated marker components, including but not limited to the receiver antennae 108, 110, the optical fiber 106, the acousto-optical sensor region that may include the FBG 116, and the piezoelectric transducer 112. In this embodiment, and as discussed above, the optical fiber 106 may extend from the catheter out the proximal end to an external light source (such as a swept laser) and a detector.

Figure 2A:
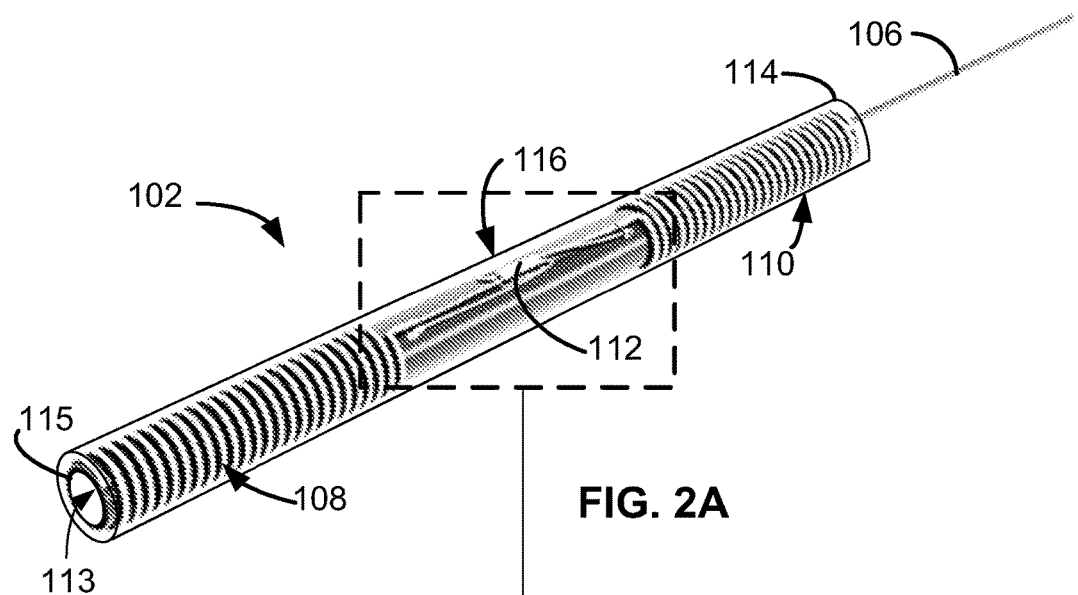
FIG. 2A is an illustration of a sleeve marker retrofit device 102, according to an exemplary embodiment of the disclosed technology.

FIG. 2A is an illustration of the sleeve marker retrofit device 102 as described above and shown in FIG. 1 (before it is installed on the catheter), according to an exemplary embodiment of the disclosed technology. In certain implementations, the retrofit device 102 may include one or more mounting tubes 115 configured to conform to an outer surface of an associated catheter (such as the catheter 104 as shown in FIG. 1) and/or to further protect the associated components of the retrofit device 102. In certain exemplary implementations, the one or more mounting tubes 115 may further provide a suitable mounting structure for the associated components, such as the receiver antennae 108, 110, the piezoelectric transducer 112, and the optical fiber 106 with the FBG 116. As described above, a catheter (or interventional probe) may be inserted into the opening 113, threaded axially through the internal hollow portion of the device 102, and secured in place.

Figure 2B:
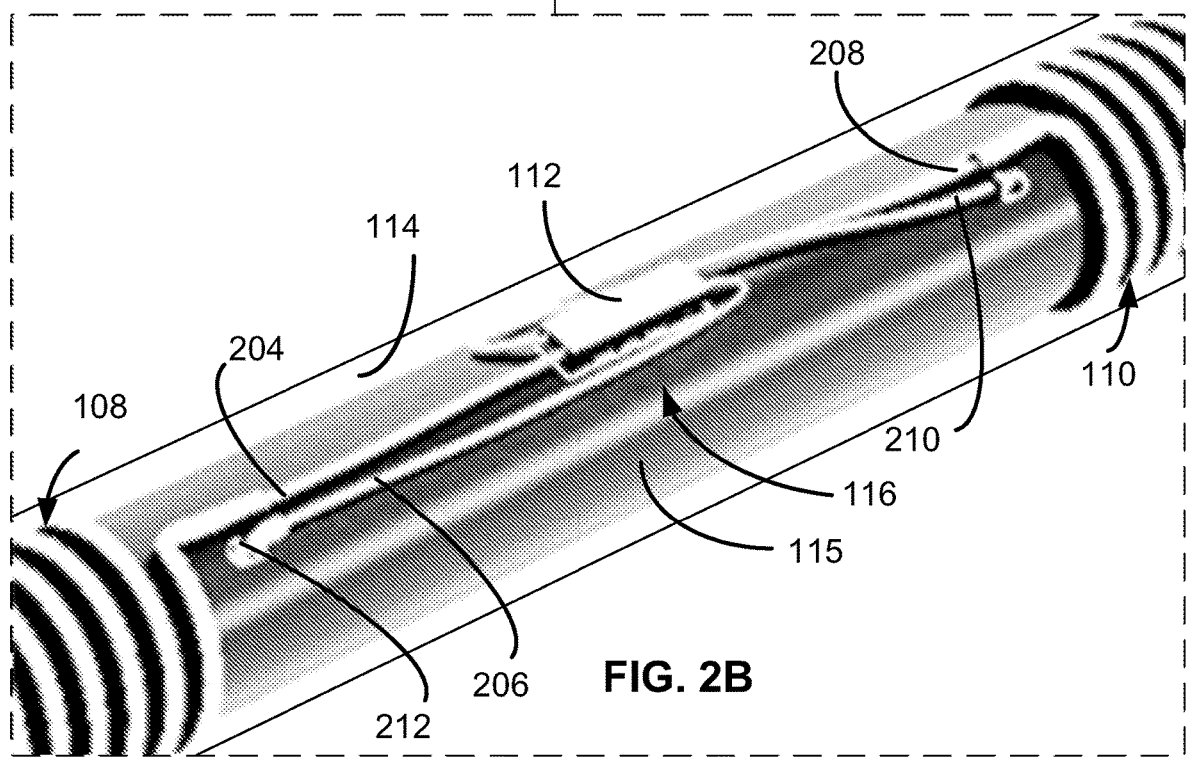
FIG. 2B is an expanded illustration showing details of the sleeve marker retrofit device as shown in the inset of FIG. 2A, according to certain exemplary embodiments of the disclosed technology.

FIG. 2B is an expanded illustration corresponding to the inset portion of FIG. 2A showing certain details of the sleeve marker retrofit device 102, according to an exemplary embodiment of the disclosed technology. In certain implementations, short leads 204, 206 may connect the antenna 108 in parallel with the piezoelectric transducer 112. In certain exemplary implementations having additional antenna 110, corresponding short leads 208, 210 may connect the additional antenna 110 in parallel with the piezoelectric transducer 112. In certain exemplary implementations, multiple antennae may be utilized to provide multiple location markers along the length of the device 102.

In certain exemplary implementations, two or more receiver antennae 108, 110 may be connected in parallel to the same piezoelectric element 112, which may be utilized to provide a measurable strain signal on the same FBG 116. In certain exemplary implementations, the two or more receiver antennae 108, 110 may be connected in parallel to separate corresponding piezoelectric elements (not shown). In certain exemplary implementations, separate piezoelectric elements may be in contact with separate FBGs (not shown), which may be connected to separate optical fibers (not shown).

With continued reference to FIG. 2B, and in embodiments that include a coil configurations for the antenna 108 (as shown), an outer coil portion of the antenna 108 may be wrapped around the outer portion of the mounting tube 115, with a first end of the antenna 108 connected to a first terminal of the piezoelectric transducer 112 by a lead 204. In an exemplary embodiment, the second end of the coil antenna 108 may be inserted radially through a first small hole (not shown) in the mounting tube 115 (and towards the central hollow portion), routed back towards the piezoelectric transducer 112, inserted outwardly through a second small hole 212, and connected to a second terminal of the piezoelectric transducer 112 via a second lead 206. In this respect, the mounting tube 115 may act as an insulator to electrically separate the leads from the coil portions. In certain exemplary implementations, another central inner tube (not shown) may be utilized as a buffer between the antenna leads and the catheter.

Figure 3:
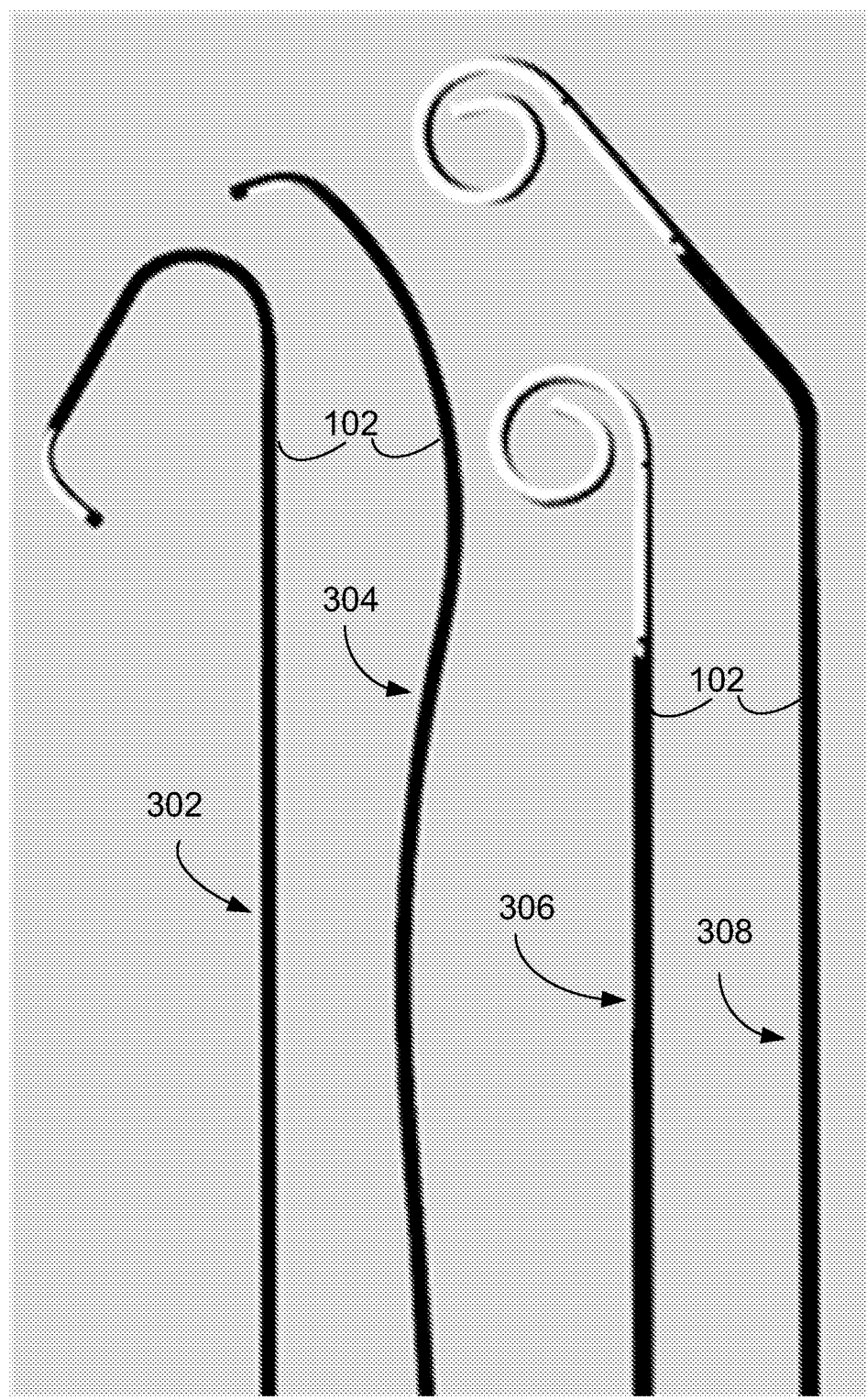
FIG. 3 is a representative illustration of a set of diagnostic angio catheters that may be suitable for accepting the sleeve marker retrofit device, according to an exemplary embodiment of the disclosed technology.

FIG. 3 is a representative illustration of a set of diagnostic angio catheters that may be suitable for accepting a sleeve marker retrofit device 102, according to certain embodiments of the disclosed technology. For example, catheter configurations, including but not limited to a Judkins Left 302, Judkins Right 304, Straight Pigtail 306, and/or 145-degree pigtail 308 may be suitable catheters for accepting the device 102. The retrofit device 102 with single or multiple receiver coils can be embedded into a flexible sleeve made of medical grade thermoplastic heat shrink tubing. In certain exemplary implementations, the sleeve can cover the entire catheter. In accordance with certain exemplary implementations of the disclosed technology, the sleeve can be advanced over any commercial MRI compatible catheter and fixed on their shafts by applying heat through a low-temperature heat gun.

Figure 4A:
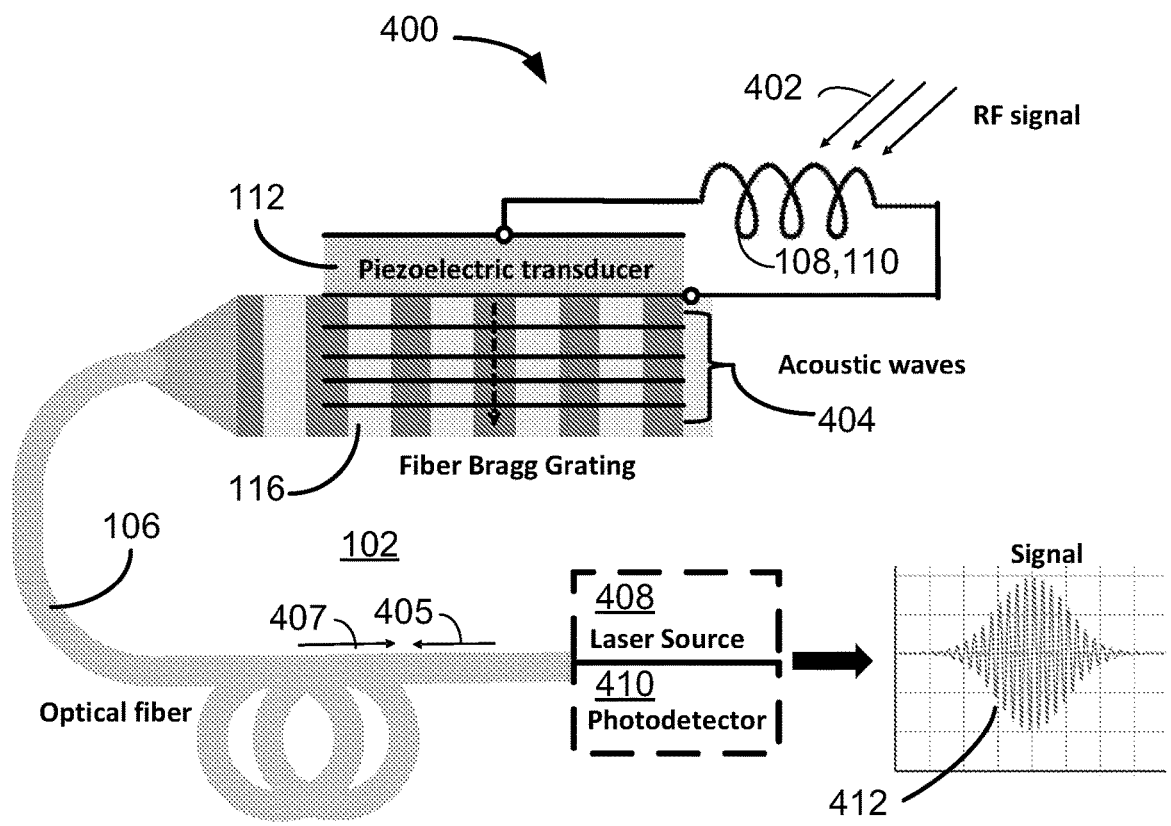
FIG. 4A is a schematic illustration of an acousto-optical sensor system, according to an exemplary implementation of the disclosed technology.

FIG. 4A is a schematic illustration of an acousto-optical sensor system 400, according to an exemplary implementation of the disclosed technology. The system 400 may include the acousto-optical sleeve marker retrofit device 102 (as discussed above) in communication with a laser source 408 and photodetector assembly 410. One or more of the antennae 108, 110 may receive RF signals 402 (from the MRI system) to produce acoustic waves 404 via the piezoelectric transducer 112. In this exemplary embodiment, a Fiber Bragg Grating (FBG) 116 may be used to enhance the detection sensitivity of the generated acoustic waves 404. The acoustic waves 404 may modulate the Bragg wavelength of the FBG 116. (Note, the FBG 116 is shown expanded in FIG. 4A for clarity).

In certain exemplary implementations, light 405 emitted from the laser source 406 (such as a swept laser) may traverse the optical fiber 106 and a portion of the incident light may be reflected (as a function of wavelength) by the FBG 116 such that reflected light 407 is modulated corresponding to the RF signal 402 frequency, the wavelength of the laser source 408, and as a function of the reflectivity curve (see FIG. 4B) of the FBG 116 to produce an output signal 412. In certain exemplary implementations, the frequency of the output signal 412 may correspond to the position(s) of the antenna(e) 108, 110 in the MRI gradient field, and thus, may be processed to provide corresponding markers for the catheter position.

According to another exemplary implementation of the disclosed technology (not shown), the piezoelectric transducer 112 may be mechanically coupled directly to the optical fiber 106. In this embodiment, the corresponding acoustic waves 404 produced in the optical fiber 106 and generated by the piezoelectric transducer 112 may modulate the elastic properties of the fiber at the RF frequencies (via the AO effect) corresponding to the RF signal 402, which in turn can be detected by laser-based interferometric sensing. Because the optical fiber 106 is not conductive, the sensor is immune to RF interference and heating along its length.

Figure 4B:
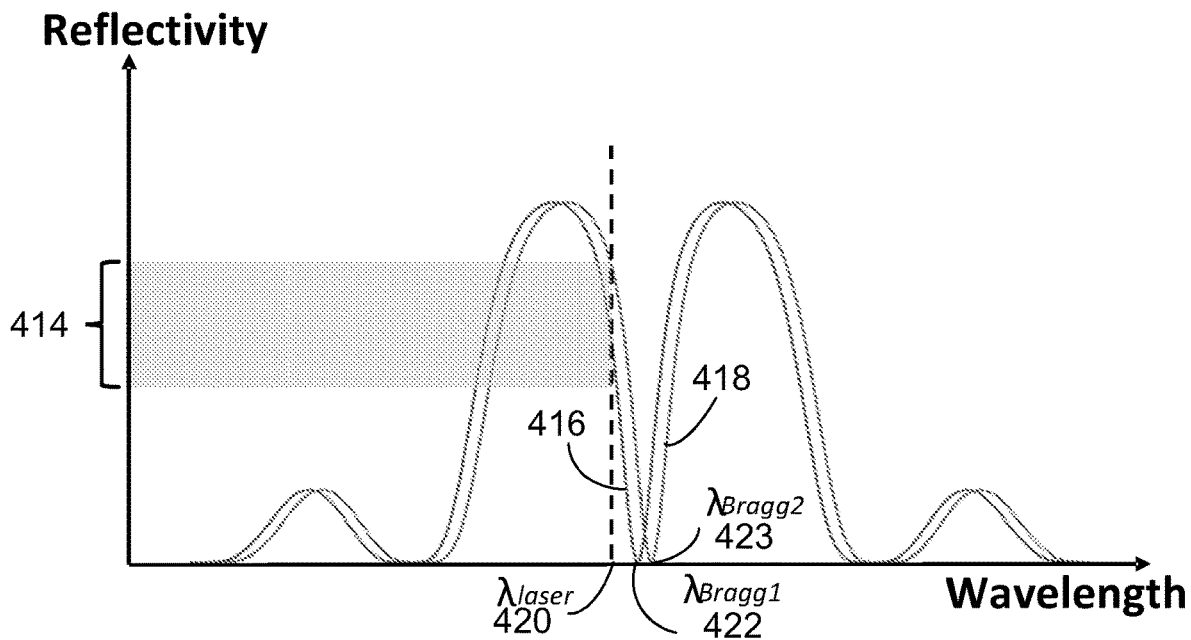
FIG. 4B illustrates the reflectivity of a fiber Bragg grating (FBG) as a function of wavelength. The reflected light intensity may be modulated by the FBG via a corresponding Bragg wavelength modulation of the FBG as induced by the received RF signal, as shown in FIG. 4A.

FIG. 4B illustrates reflectivity curves 416, 419 of the FBG 116 as a function of wavelength for two different acoustic wave 404 intensities, with continued reference to the exemplary components shown in FIG. 4A. In certain exemplary implementations, the reflected light 407 intensity may be modulated by the FBG 116 via the received RF signal 402 and the piezoelectric transducer 112. The light 405 output of the laser source 408 (for this illustration) may have a wavelength 420 fixed at or near a maximum slope of the reflectivity curve 416 to maximize the signal output. As the acoustic wave 404 modulates the FBG 116, the Bragg wavelength (and associated curves 416, 419) of the FBG 116 may oscillate between a first Bragg wavelength 422 and a second Bragg wavelength 423, thus modulating the intensity of the reflected light 407 over a range 414 corresponding to the wavelength shift in the reflectivity curves 416, 419.

Referring back to FIG. 1, by using a single RF receiver antenna 108 installed in the acousto-optical sleeve marker retrofit device 102, a location of a single point on the catheter, such as the tip, can be tracked. However, it would useful to display, for example, the orientation of the catheter 104 in addition to the position of its tip 105. This can be achieved in several ways. One embodiment can use multiple RF antennae 108, 110 connected to the same piezoelectric transducer 112 and driving the same FBG 116. Since the antennae locations over the device 102 would be different, received RF signals from each antennae containing the location information may be additive, and the location of each antenna can be obtained by analyzing the resulting received RF signal. In certain exemplary implementations, more than two antennae may be used to determine the shaft orientation of the catheter.

Figure 5A:
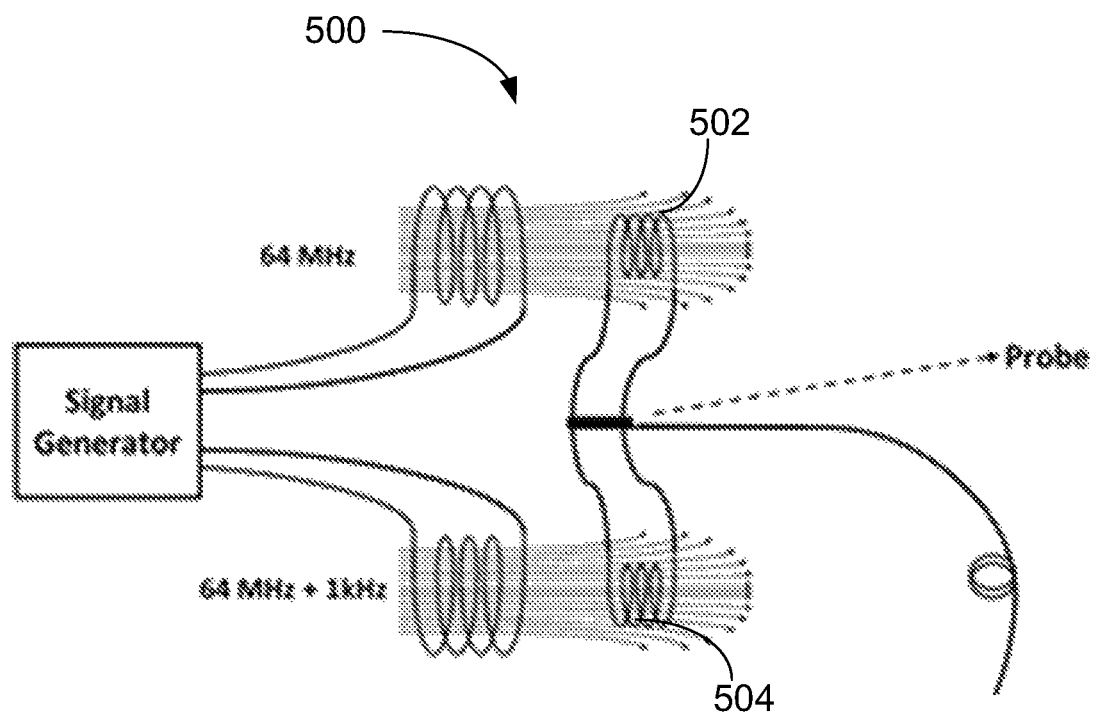
FIG. 5A is an illustration of an experimental setup where two receiver antenna (coils) are connected to the same acousto-optical sensor probe. Multiple antennae may be utilized for providing enhanced location and/or orientation information related to the probe, according to an exemplary implementation of the disclosed technology.

FIG. 5A is an illustration of an experimental setup 500 where two receiver antennae (coils, in this instance) 502, 504 are connected to the same acousto-optical sensor probe. RF signals at 64 MHz and 64.001 MHz were produced and transmitted through the air to the antennae 502, 504. This 1 kHz difference corresponds to a distance of approximately 11.7 mm under 20 mT/meter gradient field.

Figure 5B:
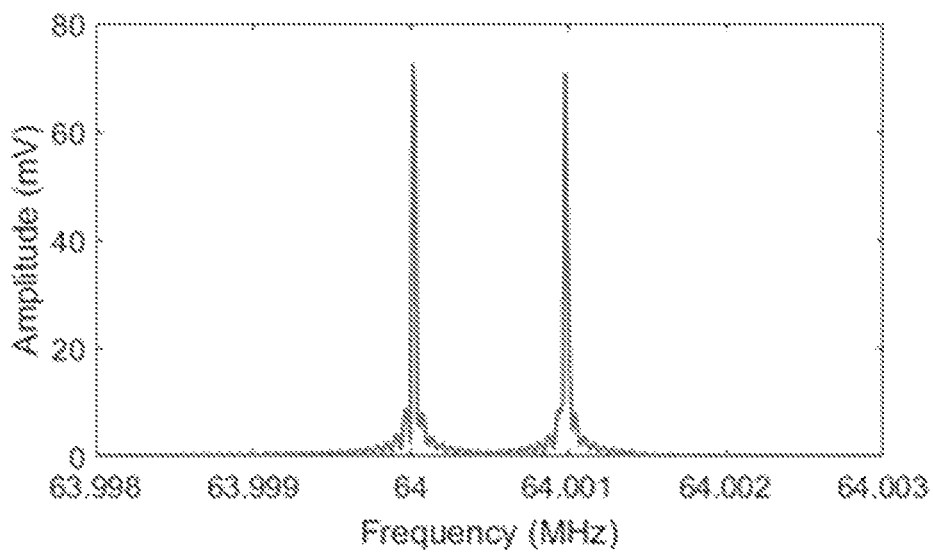
FIG. 5B illustrates the output signal of the experimental setup as depicted in FIG. 5A. Two distinct peaks (at the expected frequencies) are depicted, each of which may be utilized to locate the corresponding antennae of the probe using a single acousto-optical sensor, according to an exemplary implementation of the disclosed technology.

FIG. 5B illustrates the output signal of the experimental setup 500 as depicted in FIG. 5A. Two distinct peaks (at the expected frequencies) are depicted, each of which may be utilized to locate the corresponding antennae of the probe using a single acousto-optical sensor, according to an exemplary implementation of the disclosed technology.

As discussed above with respect to FIG. 2B, and in accordance with certain exemplary implementations of the disclosed technology, the device 102 can include multiple antennae, each connected to separate piezoelectric transducers and a separate FBGs in series with the optical fiber, and characterized by separate Bragg wavelengths. Such an implementation may be suitable for situations where the relative locations of the antennae cannot be estimated due to the bending of the catheter etc. In this exemplary implementation, the laser may be swept over a larger wavelength range (to receive reflectance signals from each of the separate FBGs) and multiple FBG outputs can be received and analyzed. The catheter shape/position information may be obtained in three dimensions while still being immune to RF heating and interference. In some instances, there may be a limitation on how close multiple FBGs can be written in (or spliced to) an optical fiber. Therefore, in certain exemplary implementations, multiple optical fibers, each with one or more series FBGs may be utilized to provide the desired density of the markers. Such embodiments may utilize optical splitters if a single swept laser is utilized.

Figure 6:
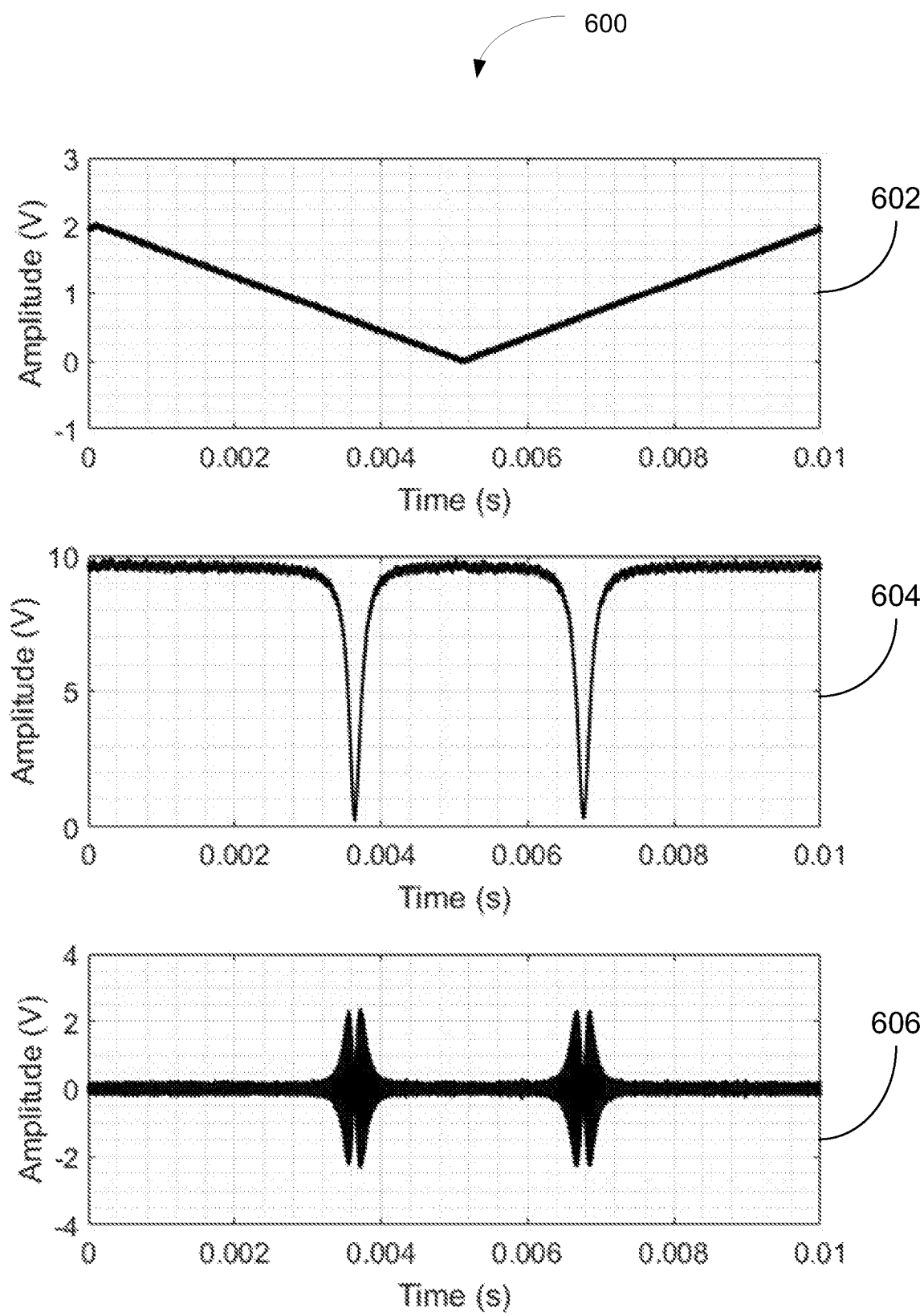
FIG. 6 illustrates experimental signals associated with a fiber Bragg grating (FBG) when a 2 MHz strain is applied to the FBG. The top chart is a sawtooth drive signal applied to a swept laser to vary the laser wavelength. The middle chart is a low-pass reflectance signal of the FBG corresponding to the swept laser. The bottom chart is a high-pass reflectance signal of the FBG showing the applied 2 MHz strain modulation, with peaks corresponding to the maximum reflectance slope of the FBG.

FIG. 6 illustrates experimental signals associated with a fiber Bragg grating (FBG) when a 2 MHz strain is applied to the FBG. The top chart is a sawtooth drive signal 602 applied to a swept laser to vary the laser output wavelength. The middle chart is a low-pass reflectance signal 604 of the FBG responsive to the incident light from a swept laser. The bottom chart is a high-pass reflectance signal 606 of the FBG showing the applied 2 MHz strain modulation, with peaks corresponding to the maximum reflectance slope of the FBG.

Figure 7A:
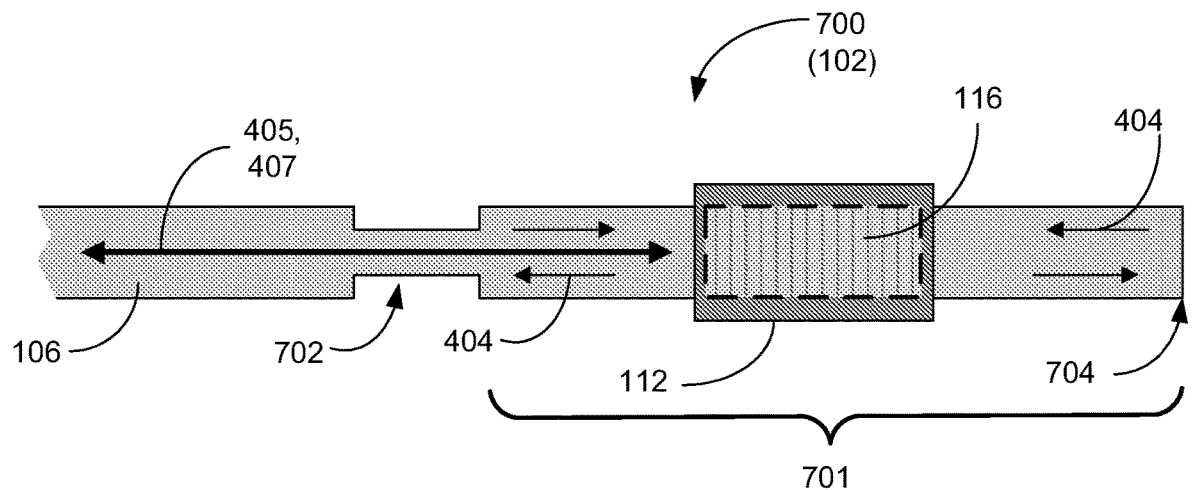
FIG. 7A depicts a portion of an enhanced acousto-optical marker device having an acoustic resonator formed by a notch in the optical fiber near the FBG region, according to an exemplary implementation of the disclosed technology.

FIG. 7A depicts a portion of an enhanced acousto-optical marker device 700, according to an exemplary embodiment (with the receiver antennae omitted for clarity). The enhanced device 700 may include an acoustic resonator 701 formed by a notch 702 in the optical fiber 106 near the (proximal side) region of the FBG 116. In accordance with certain exemplary implementations of the disclosed technology, the notch 702 may be incorporated into and utilized in the sleeve marker retrofit device 102 (as described above) to at least partially trap the acoustic wave(s) 404 generated by the piezoelectric transducer 112 and to enhance the amplitude of the acoustic wave(s) 404 that interact with the FBG 116. As discussed above with respect to the sleeve marker retrofit device 102, the FBG 116 may be covered by a piezoelectric material to form the piezoelectric transducer 112, which may be connected to an RF antenna (not shown). In certain exemplary implementations, the notch 702 may be formed by removing at least a portion of cladding from the optical fiber 106 to create an acoustic discontinuity which may reflect the acoustic wave(s) 404 back towards the distal end 704 of the optical fiber 106, where the acoustic wave(s) 404 may also be reflected to interact with the FBG 116.

Figure 7B:
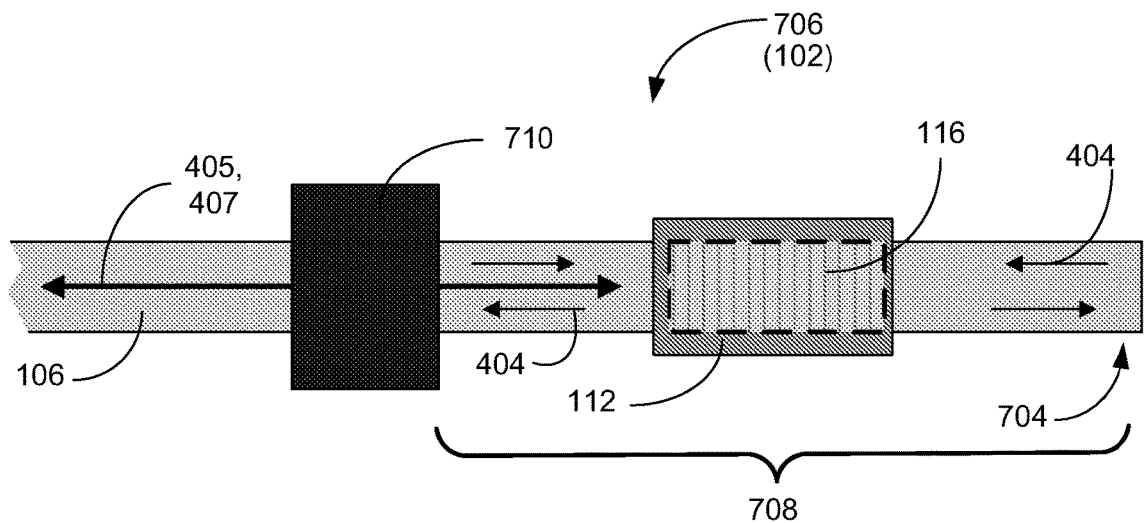
FIG. 7B depicts a portion of another embodiment of an enhanced acousto-optical marker device having an acoustic resonator formed by deposition of material on the optical fiber, according to an exemplary implementation of the disclosed technology.

FIG. 7B depicts a portion of another embodiment of an enhanced acousto-optical marker device 706 having an acoustic resonator 708 formed by application of material on the optical fiber 106, near the (proximal side) region of the FBG 116 to form a coating or ring 710 on the optical fiber 106. In accordance with certain exemplary implementations of the disclosed technology, the ring 710 may be incorporated into and utilized in the sleeve marker retrofit device 102 (as described above) to at least partially trap the acoustic wave(s) 404 generated by the piezoelectric transducer 112 and to enhance the amplitude of the acoustic wave(s) 404 that interact with the FBG 116. As discussed above with respect to the sleeve marker retrofit device 102, the FBG 116 may be covered by a piezoelectric material to form the piezoelectric transducer 112, which may be connected to an RF antenna (not shown). In certain exemplary implementations, the ring 710 may create an effective acoustical discontinuity which may reflect the acoustic wave(s) 404 back towards the distal end 704 of the optical fiber 106, where the acoustic wave(s) 404 may also be reflected to further interact with the FBG 116.

In accordance with certain exemplary implementations of the disclosed technology, the one or more of the features of the enhanced devices 700, 706, as discussed above with reference to FIG. 7A and/or FIG. 7B may be utilized to increase the sensitivity of the retrofit device 102 by creating an acoustic resonator to make more efficient use of the acoustic energy generated by the receiver antennae and piezoelectric transducer 112. The notch 702 and/or the ring 710 discontinuities may enhance acoustic wave 404 reflections, acting as a mirror for the acoustic waves 404 and effectively trapping the acoustic energy between the distal end 704 of the optical fiber 116 and the notch 702 or ring 710. Such acoustic wave 404 reflections may increase the amplitude of the strains generated in the FBG 116 region as acoustic energy builds up and result in larger acousto-optical modulation for given available electrical power from the receiver antennae, therefore increasing the sensitivity.

In certain exemplary implementations, the distance between the distal end 704 and the notch 702 or ring 710 can be optimized based on the acoustic fields generated at the Larmor frequency. Since these geometrical features are far away from the core region of the optical fiber 106, the propagating light 405, 407 and its interaction with the FBG 116 may not be adversely affected by the acoustic resonators 701, 708. There are many different ways of implementing such acoustic resonators 701, 708 such as reflectors formed by small but periodic perturbations of the refractive index of the optical fiber 106, where the periodicity is determined by the wavelength of the acoustic waves 404. In certain exemplary implementations, a quality factor of acoustic resonators 701, 708 may be adjusted so that the bandwidth of the device is still large enough to cover the typical MRI signal bandwidth of about 100 kHz.

Figure 8:
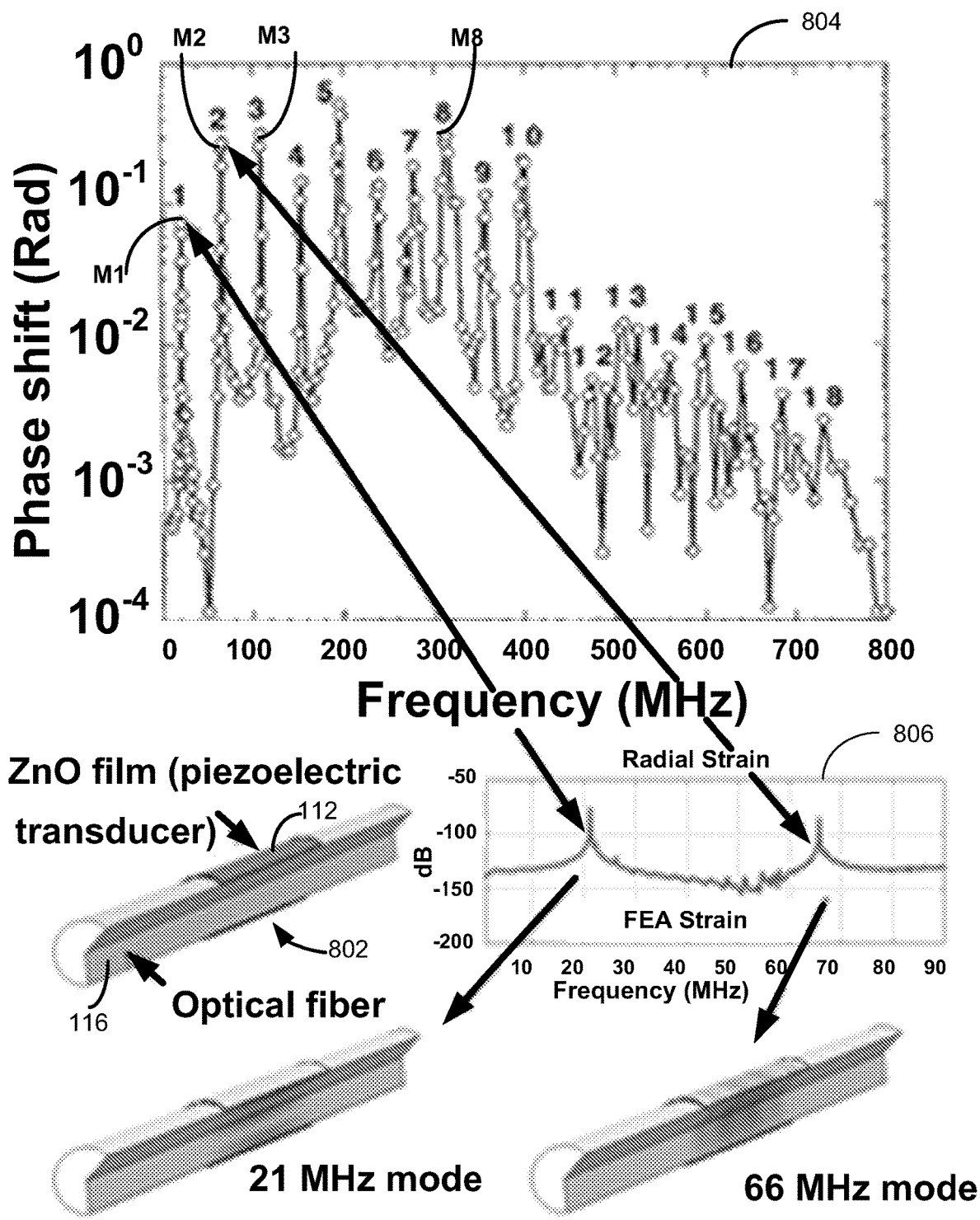
FIG. 8 depicts an acoustic resonator utilizing radial mode resonances of the optical fiber, in accordance with certain exemplary implementations of the disclosed technology.

FIG. 8 depicts cutaway views of an acoustic resonator 802 that may utilize radial mode resonances of an optical fiber 116, in accordance with certain exemplary implementations of the disclosed technology. Certain implementations of the enhanced acousto-optical marker device may utilize certain radial acoustic resonance modes of the optical fiber 106 in the region of the FBG 116 under the piezoelectric transducer 112, for example, by forming the piezoelectric transducer 112 using a thin film piezoelectric material sandwiched between thin film metal layers. The publication: "High-performance optical phase modulation using piezoelectric ZnO-coated standard telecommunication fiber," Gusarov et al., Journal of Lightwave Technology, vol. 14, pp. 2771-2777, Dec 1996, which is incorporated herein by reference as presented in full, discusses acousto-optical phase shift measurements 804 on a standard, Zinc oxide (ZnO) coated 125 μm diameter standard communication grade optical fiber. This structure has multiple radial mode resonance frequencies which are already very close to the Larmor frequencies: M1:21.6 MHz (~0.55 T), M2:66.3 MHz (~1.5 T), M3:110 MHz (close to 3 T), M8:316 MHz (~7 T). By changing the thickness of the piezoelectric coating and the metal layers forming the piezoelectric transducer 112 over the FBG 116, the radial resonances can be tuned to the desired Larmor frequency for enhanced sensitivity without a need for other modifications of the optical fiber 106 (such as the modifications discussed above with respect to FIG. 7A or FIG. 7B). The thickness values for the piezoelectric layers and metal layers can be calculated according to well-known coupled vibration formulations for a composite structure (such as the optical fiber 106 and the thin film piezoelectric transducer 112) as discussed in the abovementioned Gusarov reference. In this implementation, the section of the optical fiber 106 in the region of FBG 116 under the piezoelectric transducer 112 becomes an acoustic resonator without modifying other sections of the optical fiber. Given that the bandwidth required for MRI RF signal is about 100 kHz for 1.5 T, these resonances can provide sufficient bandwidth.

Figure 9:
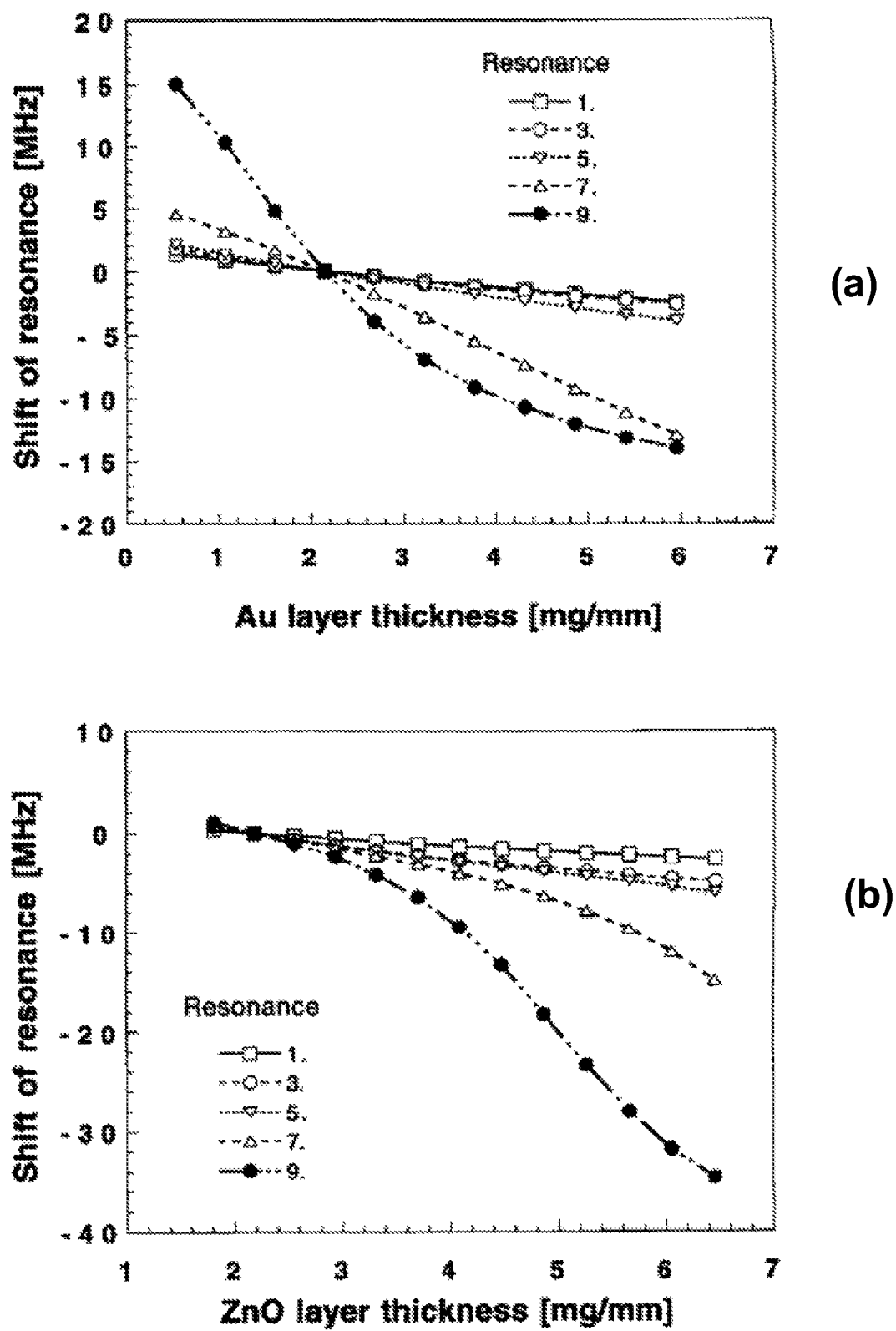
FIG. 9 depicts the resonance frequency shift as a function of (a) electrode thickness, and (b) piezoelectric layer thickness for the radial mode acoustic resonator as shown in FIG. 8, in accordance with certain exemplary implementations of the disclosed technology.

FIG. 9 depicts the resonance frequency shift (MHz) as a function of (a) electrode thickness (top graph), and (b) piezoelectric layer thickness (bottom graph) for the radial mode acoustic resonator as shown in FIG. 8, in accordance with certain exemplary implementations of the disclosed technology, and as discussed in the abovementioned Gusarov reference. In certain exemplary implementations of the disclosed technology, the radial mode acoustic resonator (such as resonator 802 shown in FIG. 8) may be configured with a length ranging from 0.5 mm to 10 mm. In certain exemplary implementations, the length may range from 10 mm to 20 mm. In certain exemplary implementations of the disclosed technology the radial mode acoustic resonator (such as resonator 802 shown in FIG. 8) may be configured with combined piezoelectric layers and metal layers having a thickness ranging from 1 micron to 20 microns. In certain exemplary implementations, the thickness may range from 20 micros to 40 microns.

Figure 10:
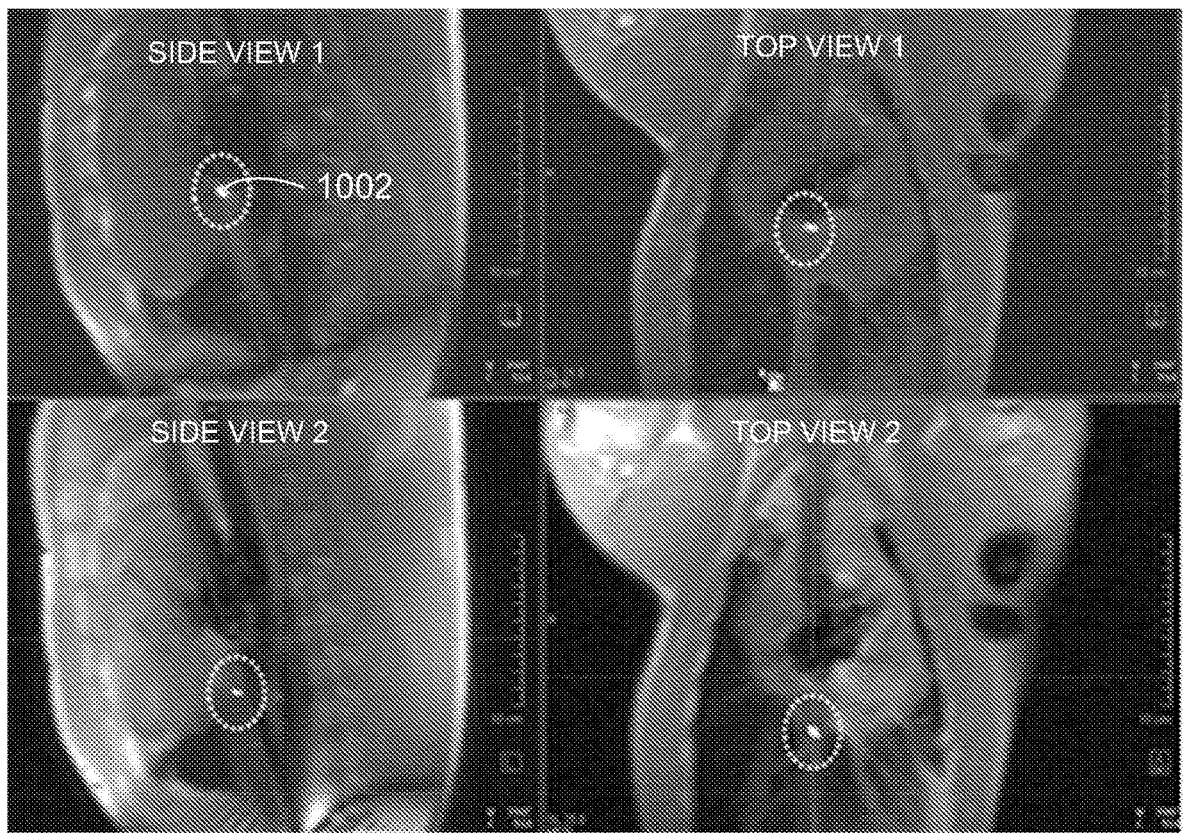
FIG. 10 shows MRI images markers in a live animal as provided by the disclosed acousto-optical probe.

FIG. 10 shows two top view and two side view MRI images of a live animal undergoing an interventional procedure using an acousto-optical marker probe device, as discussed herein. As indicated by the marker 1002, the position of the device antenna can be tracked and rendered in the MRI image based on the localized RF frequency detected at the device antenna.

Figure 11:
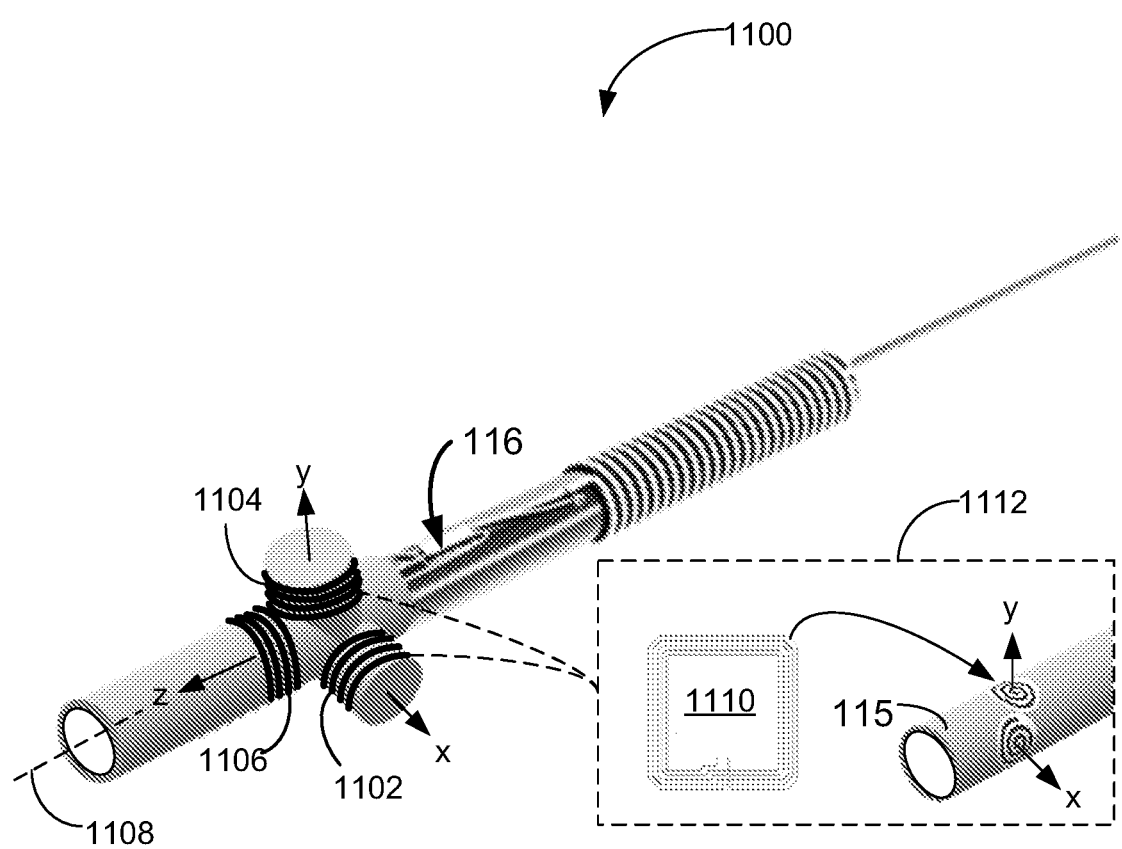
FIG. 11 is an illustration of a marker device having orthogonal antenna coils, according to an exemplary embodiment of the disclosed technology.

FIG. 11 is an illustration of a marker device 1100 (which may include features of the device 102 as discussed above) having a set of orthogonal antenna coils 1102, 1104, 1106 disposed in respective x, y, and z directions relative to the z-axis 1108 of the device 1100, according to an exemplary embodiment of the disclosed technology. Certain similar implementations may be utilized to distinguish and map different vector components of the localized MRI RF field in respective orthogonal x, y, and z directions relative to the axis 1108 of the device 1100. Certain exemplary implementations of the disclosed technology may be utilized to determine the orientation of the device 1100 during an MRI procedure. While the illustration of FIG. 11 depicts three orthogonal antennae coils 1102, 1104, 1106, certain implementations may include just two orthogonal antennae, such as the "z" coil 1106 and the "x" coil 1102.

For purposes of explanation, the "x" coil 1102 and the "y" coil 1104 are depicted in FIG. 11 as protruding orthogonally with respect to the z-axis 1108 of the device 1100, which may add to the bulk of the device 1100. To eliminate such protrusions, one or more of the antennae coils may be in the form of a patch antenna 1110 (similar to patch antennae utilized in RFID tags). In certain exemplary implementations, the patch antenna 1110 may be conformally disposed on the surface of the mounting tube 115, as depicted in the inset illustration 1112 and electrically connected (not shown) to the piezoelectric transducer 116. This configuration, when miniaturized and disposed on the wall of a catheter (for example, by heat shrinking, as previously discussed) may increase the likelihood that the device 1100 will receive sufficient MRI signal for marking its position independent of the orientation of the device 1100 with respect to the MRI RF field.

In accordance with certain exemplary implementations of the disclosed technology, the patch antenna 1110 concept may provide certain benefits in size/bulk reduction and/or ease of manufacturing and may be utilized for any of the antenna discussed herein, including but not limited to the antennae coils 108, 110, as shown in FIG. 2A and FIG. 2B.

Figure 12:
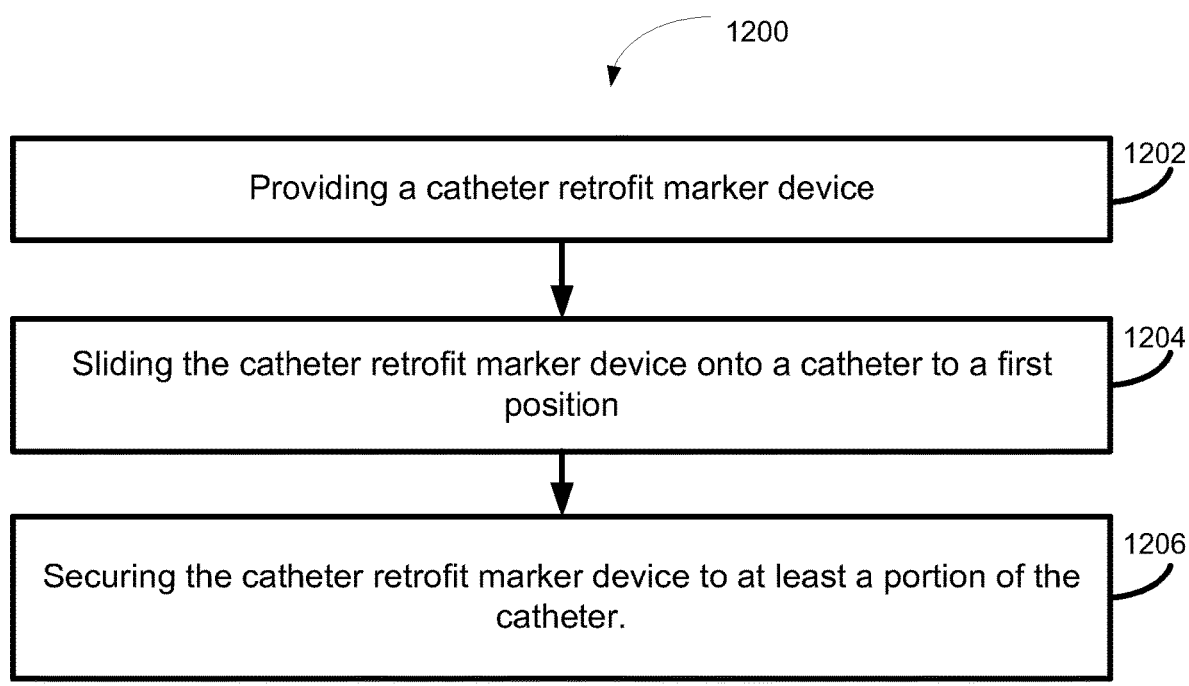
FIG. 12 is a flow diagram of a method, according to an exemplary embodiment of the disclosed technology.

FIG. 12 is a flow diagram of a method 1200, according to an exemplary embodiment of the disclosed technology. In block 1202, the method includes providing a catheter retrofit marker device. In block 1204, the method 1200 includes sliding the catheter retrofit marker device onto a catheter to a first position. In block 1206, the method 1200 includes securing the catheter retrofit marker device to at least a portion of the catheter.

In accordance with certain exemplary implementations of the disclosed technology, the catheter retrofit marker device can include a medical grade thermoplastic heat-shrink tubing. In certain example implementations, securing the catheter retrofit marker device to at least a portion of the catheter can include heating the catheter retrofit device.

Certain exemplary implementations of the disclosed technology can include interrogating, with a light source, and via the optical fiber, an acousto-optical sensor region of the catheter retrofit marker device.

Certain exemplary implementations of the disclosed technology can include detecting, with a photodetector, interrogation light reflected from the acousto-optical sensor region of catheter retrofit marker device. Certain exemplary implementations of the disclosed technology can include outputting a signal corresponding to the detected interrogation light reflected from the acousto-optical sensor region.

The disclosed technology relates to a catheter retrofit device for active MRI device location visualization. The retrofit device can include a mounting tube configured to accept a catheter and to a least partially conform to a shape of the catheter; an optical fiber including a distal end in communication with a portion of the mounting tube structure; an acousto-optical sensor region disposed at the distal end of the optical fiber; an electro-mechanical conversion assembly in communication with the acousto-optical sensor region, the electro-mechanical conversion assembly including: one or more antennae disposed on the mounting tube structure, the one or more antennae configured to receive radio-frequency (RF) electromagnetic energy and produce a corresponding electrical signal; and an ultrasonic transducer in mechanical communication with the acousto-optical sensor region, wherein the ultrasonic transducer is in electrical communication with the one or more antennae, and wherein the ultrasonic transducer is configured to elastically modulate the acousto-optical sensor region by acoustic waves generated responsive to the electrical signal received from the one or more antennae.

In certain implementations, the catheter retrofit device can include a resonator in communication with the optical fiber, wherein the resonator is configured to at least partially reflect the generated acoustic waves for enhanced modulation of the acousto-optical sensor region. In certain exemplary implementations, the resonator can include an acoustical discontinuity comprising a notch formed by removal of at least a portion of cladding from the optical fiber. In certain exemplary implementations, the resonator can include an acoustical discontinuity comprising deposition of a ring of material on the optical fiber. Yet, in certain implementations, the resonator uses radial vibration resonances of the optical fiber under the piezoelectric transducer over the FBG region.

In accordance with certain implementations of the disclosed technology, the one or more antennae can include at least a first antenna and a second antenna, wherein the second antenna may be oriented in an orthogonal direction with respect to the first antenna.

In certain exemplary implementations, the acousto-optical sensor region can include a first fiber Bragg grating (FBG) and a second FBG. In certain exemplary implementations, the electromagnetic conversion assembly can include a first piezoelectric transducer in mechanical communication with the first FBG and in electrical communication with the first antenna. The electromagnetic conversion assembly can include a second piezoelectric transducer in mechanical communication with the second FBG and in electrical communication with the second antenna.

In certain exemplary implementations, the one or more antennae can include a first antenna, a second antenna, and a third antenna. In certain exemplary implementations, the first antenna, the second antenna, and the third antenna may be configured in an orthogonal direction with respect to one another.

In accordance with certain implementations of the disclosed technology, the one or more antennae can include one or more of: a patch antenna; a coil antenna; and a dipole antenna.

Certain implementations of the catheter retrofit device can include an inner tube disposed inside the mounting tube structure, wherein the inner tube may be configured to accept and conform to the catheter. In certain exemplary implementations, one or more of the mounting tube and/or the inner tube can include a medical grade thermoplastic heat-shrink tubing.

In accordance with certain exemplary implementations of the disclosed technology, the acousto-optical sensor region can include a fiber Bragg grating (FBG).

In accordance with certain exemplary implementations of the disclosed technology, the ultrasonic transducer can include a piezoelectric transducer.

In accordance with certain exemplary implementations of the disclosed technology, the optical fiber can include at least one proximal end configured for coupling with an external light source for interrogation of the acousto-optical sensor region.

In accordance with certain exemplary implementations of the disclosed technology, the optical fiber can include at least one proximal end configured for coupling with a photodetector to receive interrogation light reflected from the acousto-optical sensor region.

In accordance with certain exemplary implementations of the disclosed technology, the optical fiber, and the electromechanical conversion assembly are configured to reduce MRI RF-induced heating of the device.

The disclosed technology can include a catheter retrofit system for MRI active device location visualization. The system can include a retrofitted interventional probe that includes: a mounting tube configured to accept a catheter and to a least partially conform to a shape of the catheter; an optical fiber including a distal end in communication with a portion of the mounting tube structure; an acousto-optical sensor region disposed at the distal end of the optical fiber; an electro-mechanical conversion assembly in communication with the acousto-optical sensor region, the electro-mechanical conversion assembly including: one or more antennae disposed on the mounting tube structure, the one or more antennae configured to receive radio-frequency (RF) electromagnetic energy and produce a corresponding electrical signal; and an ultrasonic transducer in mechanical communication with the acousto-optical sensor region, wherein the ultrasonic transducer is in electrical communication with the one or more antennae, and wherein the ultrasonic transducer is configured to elastically modulate the acousto-optical sensor region by acoustic waves generated responsive to the electrical signal received from the one or more antennae. The catheter retrofit system can include a mechanical-optical conversion assembly in communication with a proximal end of the optical fiber, the mechanical-optical conversion assembly can include: a light source coupled to the proximal end of the optical fiber and configured to interrogate the acousto- optical sensor region; and a photodetector coupled to the proximal end of the optical fiber, the photodetector configured to receive interrogation light reflected from the acousto-optical sensor region.

In certain exemplary implementations, acousto-optical sensor region and/or the optical fiber may include a resonator that can be configured to at least partially reflect the generated acoustic waves to enhance a modulation amplitude of the acousto-optical sensor region. In certain implementations, the resonator includes an acoustical discontinuity that can include one or more of: a notch formed by removal of at least a portion of cladding from the optical fiber, and deposition of a material on the optical fiber. In some embodiments, the piezoelectric thin film transducer on the fiber can serve as the resonator using the radial vibration modes of the composite optical fiber/thin film transducer structure.

In accordance with certain exemplary implementations of the disclosed technology, the one or more antennae can include one or more of a first antenna and a second antenna. In certain example implementations, the second antenna may be oriented in an orthogonal direction with respect to the first antenna.

In certain implementations, the acousto-optical sensor region can include a first fiber Bragg grating (FBG) and a second FBG. In certain exemplary embodiments, the electromagnetic conversion assembly can include a first piezoelectric transducer in mechanical communication with the first FBG and in electrical communication with one or more of the first antenna and the second antenna. In certain example implementations, the electromagnetic conversion assembly can include a second piezoelectric transducer in mechanical communication with the second FBG and in electrical communication with the second antenna.

Numerous specific details of the disclosed technology are set forth herein. However, it is to be understood that implementations of the disclosed technology may be practiced without these specific details. In other instances, well-known methods, structures, and techniques have not been shown in detail in order not to obscure an understanding of this description. References to "one implementation," "an implementation," "exemplary implementation," "various implementations," etc., indicate that the implementation(s) of the disclosed technology so described may include a particular feature, structure, or characteristic, but not every implementation necessarily includes the particular feature, structure, or characteristic. Further, repeated use of the phrase "in one implementation" does not necessarily refer to the same implementation, although it may. The use of "exemplary" herein carries the same meaning as "example," and is not intended to mean "preferred" or "best."

Throughout the specification and the claims, the following terms take at least the meanings explicitly associated herein, unless the context clearly dictates otherwise. The term "connected" means that one function, feature, structure, or characteristic is directly joined to or in communication with another function, feature, structure, or characteristic. The term "coupled" means that one function, feature, structure, or characteristic is directly or indirectly joined to or in communication with another function, feature, structure, or characteristic. The term "or" is intended to mean an inclusive "or." Further, the terms "a," "an," and "the" are intended to mean one or more unless specified otherwise or clear from the context to be directed to a singular form.

As used herein, unless otherwise specified the use of the ordinal adjectives "first," "second," "third," etc., to describe a common object, merely indicate that different instances of like objects are being referred to and are not intended to imply that the objects so described must be in a given sequence, either temporally, spatially, in ranking, or in any other manner.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described as making up the various elements of the invention are intended to be illustrative and not restrictive. Many suitable materials that would perform the same or a similar function as the materials described herein are intended to be embraced within the scope of the invention. Such other materials not described herein can include but are not limited to, for example, materials that are developed after the time of the development of the invention.

While certain implementations of the disclosed technology have been described in connection with what is presently considered to be the most practical and various implementations, it is to be understood that the disclosed technology is not to be limited to the disclosed implementations, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain implementations of the disclosed technology, including the best mode, and to enable any person skilled in the art to practice certain implementations of the disclosed technology, including making and using any devices or systems and performing any incorporated methods. The patentable scope of certain implementations of the disclosed technology is defined in the claims and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A catheter retrofit system for active magnetic resonance imaging (MRI) device location visualization comprising:
   a mounting tube configured to accept a catheter and to a least partially conform to a shape of the catheter;
   a non-conductive optical fiber with a distal end in communication with a portion of the mounting tube, a proximal end, and an acousto-optical sensor region disposed in proximity to the distal end and comprising a first fiber Bragg grating (FBG);
   an electro-mechanical conversion assembly comprising:
      a first antenna disposed on the mounting tube and configured to receive radio-frequency (RF) electromagnetic energy and produce a corresponding electrical signal; and
      a first piezoelectric transducer in mechanical communication with the first FBG, and in electrical communication with the first antenna;
      wherein the first piezoelectric transducer is configured to modulate elastic properties of the acousto-optical sensor region with acoustic waves generated responsive to the electrical signal received from the first antenna; and
   an acoustic resonator in communication with the optical fiber and configured to at least partially reflect the generated acoustic waves for enhanced modulation of the acousto-optical sensor region;
   wherein characteristics of the modulated elastic properties of the optical fiber are detectable at the proximal end of the optical fiber; and
   wherein at least the optical fiber and the electro-mechanical conversion assembly are configured to reduce MRI RF-induced heating of the system.

2. The system of claim 1, wherein the acoustic resonator comprises an acoustical discontinuity comprising a notch formed by removal of at least a portion of cladding from the optical fiber.

3. The system of claim 1, wherein the acoustic resonator comprises an acoustical discontinuity formed by deposition of a ring of material on the optical fiber.

4. A system for active magnetic resonance imaging (MRI) device location visualization comprising:
   a non-conductive optical fiber with a distal end, a proximal end, and an acousto-optical sensor region disposed in proximity to the distal end and comprising a first fiber Bragg grating (FBG); and
   an electro-mechanical conversion assembly comprising:
      a first antenna configured to receive radio-frequency (RF) electromagnetic energy and produce a corresponding electrical signal; and
      a first piezoelectric transducer in mechanical communication with the first FBG, and in electrical communication with the first antenna;
      wherein the first piezoelectric transducer is configured to modulate elastic properties of the acousto-optical sensor region with acoustic waves generated responsive to the electrical signal received from the first antenna; and wherein at least a thickness dimension of the first piezoelectric transducer is configured to produce one or more resonance frequencies corresponding with one or more Larmor frequencies;

wherein characteristics of the modulated elastic properties of the optical fiber are detectable at the proximal end of the optical fiber; and wherein at least the optical fiber and the electro-mechanical conversion assembly are configured to reduce MRI RF-induced heating of the system.

5. The system of claim 1, wherein the electro-mechanical conversion assembly further comprises a second antenna; and wherein the second antenna is oriented in an orthogonal direction with respect to the first antenna.

6. A system for active magnetic resonance imaging (MRI) device location visualization comprising:

a non-conductive optical fiber with a distal end, a proximal end, and an acousto-optical sensor region disposed in proximity to the distal end and comprising a first fiber Bragg grating (FBG) and a second FBG; and an electro-mechanical conversion assembly comprising:
a first antenna configured to receive radio-frequency (RF) electromagnetic energy and produce a corresponding electrical signal;
a second antenna oriented in an orthogonal direction with respect to the first antenna:
a first piezoelectric transducer in mechanical communication with the first FBG, and in electrical communication with the first antenna; and
a second piezoelectric transducer in mechanical communication with the second FBG and in electrical communication with the second antenna;
wherein the first piezoelectric transducer is configured to modulate elastic properties of the acousto-optical sensor region with acoustic waves generated responsive to the electrical signal received from the first antenna;
wherein characteristics of the modulated elastic properties of the optical fiber are detectable at the proximal end of the optical fiber; and
wherein at least the optical fiber and the electro-mechanical conversion assembly are configured to reduce MRI RF-induced heating of the system.

7. The system of claim 5, wherein the electro-mechanical conversion assembly further comprises a third antenna; and
wherein the first antenna, the second antenna, and the third antenna are configured in an orthogonal direction with respect to one another.

8. The system of claim 5, wherein at least one of the antennae comprises a patch antenna.

9. The system of claim 5, wherein at least one of the antennae comprises a coil antenna.

10. The system of claim 1 further comprising an inner tube disposed inside the mounting tube, wherein the inner tube is configured to accept and conform to the catheter.

11. The system of claim 10, wherein one or more of the mounting tube and the inner tube comprises a medical grade thermoplastic heat-shrink tubing.

12. The system of claim 1 further comprising an external light source;
wherein the proximal end of the optical fiber is configured for coupling with the external light source for interrogation of the acousto-optical sensor region.

13. The system of claim 1 further comprising a photodetector;

wherein the proximal end of the optical fiber is configured for coupling with the photodetector to receive interrogation light reflected from the acousto-optical sensor region.

14. A catheter retrofit system for magnetic resonance imaging (MRI) active device location visualization, the system comprising:
a retrofitted interventional probe comprising:
a mounting tube configured to accept a catheter and to a least partially conform to a shape of the catheter;
an optical fiber including a distal end in communication with a portion of the mounting tube; and
an acousto-optical sensor region disposed at the distal end of the optical fiber, the acousto-optical sensor region including an electro-mechanical conversion assembly comprising:
one or more antennae disposed on the mounting tube and configured to receive radio-frequency (RF) electromagnetic energy and produce a corresponding electrical signal; and
a radial mode resonator in mechanical communication with the acousto-optical sensor region, wherein the radial mode resonator is in electrical communication with one or more of the antennae, wherein the radial mode resonator is configured to modulate elastic properties of the acousto-optical sensor region with acoustic waves generated responsive to the electrical signal received from the one or more antennae, and wherein at least a thickness dimension of the radial mode resonator is configured to produce one or more resonance frequencies corresponding with one or more Larmor frequencies; and
a mechanical-optical conversion assembly in communication with a proximal end of the optical fiber, the mechanical-optical conversion assembly including:
a light source coupled to the proximal end of the optical fiber and configured to interrogate the acousto-optical sensor region; and
a photodetector coupled to the proximal end of the optical fiber, the photodetector configured to receive interrogation light reflected from the acousto-optical sensor region.

15. The system of claim 14 further comprising an acoustic resonator in communication with the optical fiber;
wherein the acoustic resonator is configured to at least partially reflect the generated acoustic waves to enhance a modulation amplitude of the acousto-optical sensor region; and
wherein the acoustic resonator comprises an acoustical discontinuity comprising one or more of:
a notch formed by removal of at least a portion of cladding from the optical fiber; or
deposition of a material on the optical fiber.

16. The system of claim 14, wherein the one or more antennae comprise at least a first antenna and a second antenna; and
wherein the second antenna is oriented in an orthogonal direction with respect to the first antenna.

17. A catheter retrofit system for magnetic resonance imaging (MRI) active device location visualization, the system comprising:
a retrofitted interventional probe comprising:
a mounting tube configured to accept a catheter and to a least partially conform to a shape of the catheter;
an optical fiber including a distal end in communication with a portion of the mounting tube; and an acousto-optical sensor region disposed at the distal end of the optical fiber and comprising a first fiber Bragg grating (FBG) and a second FBG;
wherein the acousto-optical sensor region includes an electro-mechanical conversion assembly comprising:
a first antenna and a second antenna, each disposed on the mounting tube and configured to receive radio-frequency (RF) electromagnetic energy and produce a corresponding electrical signal;
a first piezoelectric transducer in mechanical communication with the first FBG and in electrical communication with the first antenna; and
a second piezoelectric transducer in mechanical communication with the second FBG and in electrical communication with the second antenna;
wherein the first and second piezoelectric transducers are configured to modulate elastic properties of the acousto-optical sensor region with acoustic waves generated responsive to the electrical signal received from the first and second antennae; and
a mechanical-optical conversion assembly in communication with a proximal end of the optical fiber, the mechanical-optical conversion assembly including:
a light source coupled to the proximal end of the optical fiber and configured to interrogate the acousto-optical sensor region; and
a photodetector coupled to the proximal end of the optical fiber, the photodetector configured to receive interrogation light reflected from the acousto-optical sensor region.

18. The system of claim 14, wherein the one or more antennae comprise one or more of:
a patch antenna;
a coil antenna; or
a dipole antenna.

19. A catheter for active magnetic resonance imaging (MRI) device location visualization, the catheter comprising the system of claim 1.

20. A marker device for active magnetic resonance imaging (MRI) device location visualization, the marker device comprising:
the system of claim 1; and
a resonator in communication with the optical fiber, wherein the resonator is configured to enhance a modulation amplitude of the acousto-optical sensor region.

21. A marker device for active magnetic resonance imaging (MRI) device location visualization, the marker device comprising:
a system comprising:
a non-conductive optical fiber with a distal end, a proximal end, and an acousto-optical sensor region disposed in proximity to the distal end and comprising a first fiber Bragg grating (FBG); and
an electro-mechanical conversion assembly comprising:
a first antenna configured to receive radio-frequency (RF) electromagnetic energy and produce a corresponding electrical signal; and
a first piezoelectric transducer in mechanical communication with the first FBG, and in electrical communication with the first antenna;
wherein the first piezoelectric transducer is configured to modulate elastic properties of the acousto-optical sensor region with acoustic waves generated responsive to the electrical signal received from the first antenna:
wherein characteristics of the modulated elastic properties of the optical fiber are detectable at the proximal end of the optical fiber; and
wherein at least the optical fiber and the electro-mechanical conversion assembly are configured to reduce MRI RF-induced heating of the system; and
a resonator in communication with the optical fiber;
wherein the resonator is configured to:
enhance a modulation amplitude of the acousto-optical sensor region; and
at least partially reflect the generated acoustic waves to enhance a modulation amplitude of the acousto-optical sensor region; and
wherein the resonator comprises an acoustical discontinuity comprising one or more of:
a notch formed by removal of at least a portion of cladding from the optical fiber; or
deposition of a material on the optical fiber.

22. A marker device for active magnetic resonance imaging (MRI) device location visualization, the marker device comprising:
a system comprising:
a non-conductive optical fiber with a distal end, a proximal end, and an acousto-optical sensor region disposed in proximity to the distal end and comprising a first fiber Bragg grating (FBG); and
an electro-mechanical conversion assembly comprising:
a first antenna configured to receive radio-frequency (RF) electromagnetic energy and produce a corresponding electrical signal; and
a first piezoelectric transducer in mechanical communication with the first FBG, and in electrical communication with the first antenna;
wherein the first piezoelectric transducer is configured to modulate elastic properties of the acousto-optical sensor region with acoustic waves generated responsive to the electrical signal received from the first antenna:
wherein characteristics of the modulated elastic properties of the optical fiber are detectable at the proximal end of the optical fiber; and
wherein at least the optical fiber and the electro-mechanical conversion assembly are configured to reduce MRI RF-induced heating of the system; and
a resonator in communication with the optical fiber and configured to enhance a modulation amplitude of the acousto-optical sensor region;
wherein the resonator comprises a radial mode resonator in communication with the acousto-optical sensor region of the optical fiber; and
wherein at least a thickness dimension of the radial mode resonator is configured to produce one or more resonance frequencies corresponding with one or more Larmor frequencies.

23. A method comprising:
sliding the marker device of claim 22 onto a catheter to a first position;
securing the marker device to at least a portion of the catheter;
interrogating, with a light source, and via the optical fiber, the acousto-optical sensor region;
detecting, with a photodetector, interrogation light reflected from the acousto-optical sensor region; and
outputting a signal corresponding to the detected interrogation light reflected from the acousto-optical sensor region.

24. The method of claim 23, wherein securing the marker device to at least a portion of the catheter comprises heating at least a portion of a mounting tube of the marking device configured to accept the catheter and to a least partially conform to a shape of the catheter; and
wherein the mounting tube comprises a medical grade thermoplastic heat-shrink tubing.

25. A catheter retrofit device comprising:
a mounting tube configured to accept a catheter and to a least partially conform to a shape of the catheter;
an optical fiber including a distal end in communication with at least a portion of the mounting tube; and
an acousto-optical sensor region disposed at the distal end of the optical fiber comprising:
a first fiber Bragg grating (FBG);
a second FBG;
a first antenna;
a second antenna;
a first piezoelectric transducer in mechanical communication with the first FBG and in electrical communication with the first antenna; and
a second piezoelectric transducer in mechanical communication with the second FBG and in electrical communication with the second antenna.

26. A catheter retrofit device for active magnetic resonance imaging (MRI) device location visualization, the retrofit device comprising:
a mounting tube configured to accept a catheter and to a least partially conform to a shape of the catheter;
an optical fiber including a distal end in communication with a portion of the mounting tube
a resonator in communication with the optical fiber; and
an acousto-optical sensor region disposed at the distal end of the optical fiber, the acousto-optical sensor region including an electro-mechanical conversion assembly comprising:
one or more antennae disposed on the mounting tube and configured to receive radio-frequency (RF) electromagnetic energy and produce a corresponding electrical signal; and
an ultrasonic transducer in mechanical communication with the acousto-optical sensor region, and in electrical communication with one or more of the antennae, the ultrasonic transducer configured to modulate elastic properties of the acousto-optical sensor region with acoustic waves generated responsive to the electrical signal received from one or more of the antennae;
wherein the resonator is configured to at least partially reflect the generated acoustic waves for enhanced modulation of the acousto-optical sensor region; and
wherein the resonator comprises an acoustical discontinuity comprising a notch formed by removal of at least a portion of cladding from the optical fiber.

27. A catheter retrofit device for active magnetic resonance imaging (MRI) device location visualization, the retrofit device comprising:
a mounting tube configured to accept a catheter and to a least partially conform to a shape of the catheter;
an optical fiber including a distal end in communication with a portion of the mounting tube;
a radial mode resonator; and
an acousto-optical sensor region disposed at the distal end of the optical fiber, the acousto-optical sensor region including an electro-mechanical conversion assembly comprising:
one or more antennae disposed on the mounting tube and configured to receive radio-frequency (RF) electromagnetic energy and produce a corresponding electrical signal; and
an ultrasonic transducer in mechanical communication with the acousto-optical sensor region, and in electrical communication with one or more of the antennae, the ultrasonic transducer configured to modulate elastic properties of the acousto-optical sensor region with acoustic waves generated responsive to the electrical signal received from one or more of the antennae;
wherein the radial mode resonator is in communication with the acousto -optical sensor region of the optical fiber; and
wherein at least a thickness dimension of the radial mode resonator is configured to produce one or more resonance frequencies corresponding with one or more Larmor frequencies.

28. A catheter retrofit device for active magnetic resonance imaging (MRI) device location visualization, the retrofit device comprising:
a mounting tube configured to accept a catheter and to a least partially conform to a shape of the catheter;
an optical fiber including a distal end in communication with a portion of the mounting tube; and
an acousto-optical sensor region disposed at the distal end of the optical fiber and comprising a first fiber Bragg grating (FBG) and a second FBG;
wherein the acousto-optical sensor region includes an electro-mechanical conversion assembly comprising:
a first antenna and a second antenna, each disposed on the mounting tube and configured to receive radio-frequency (RF) electromagnetic energy and produce a corresponding electrical signal;
a first piezoelectric transducer in mechanical communication with the first FBG and in electrical communication with the first antenna; and
a second piezoelectric transducer in mechanical communication with the second FBG and in electrical communication with the second antenna;
wherein the first and second piezoelectric transducers are configured to modulate elastic properties of the acousto-optical sensor region with acoustic waves generated responsive to the electrical signal received from the first and second antennae.

* * * * *